(12) United States Patent
Winter et al.

(10) Patent No.: US 9,255,327 B2
(45) Date of Patent: Feb. 9, 2016

(54) THERMALLY STABLE VOLATILE PRECURSORS

(75) Inventors: Charles H. Winter, Bloomfield Hills, MI (US); Thomas J. Knisley, Monroe, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 13/818,154

(22) PCT Filed: Aug. 23, 2011

(86) PCT No.: PCT/US2011/048792
§ 371 (c)(1),
(2), (4) Date: Feb. 21, 2013

(87) PCT Pub. No.: WO2012/027357
PCT Pub. Date: Mar. 1, 2012

(65) Prior Publication Data
US 2013/0164456 A1    Jun. 27, 2013

Related U.S. Application Data

(60) Provisional application No. 61/376,495, filed on Aug. 24, 2010.

(51) Int. Cl.
C07F 15/06 (2006.01)
C23C 16/34 (2006.01)
B05D 3/10 (2006.01)
C07F 11/00 (2006.01)
C07F 13/00 (2006.01)
C07F 15/02 (2006.01)
C07F 15/04 (2006.01)

(52) U.S. Cl.
CPC ............... C23C 16/34 (2013.01); B05D 3/107 (2013.01); C07F 11/005 (2013.01); C07F 13/005 (2013.01); C07F 15/025 (2013.01); C07F 15/045 (2013.01); C07F 15/065 (2013.01)

(58) Field of Classification Search
None
See application file for complete search history.

(56) References Cited

U.S. PATENT DOCUMENTS

| | | |
|---|---|---|
| 3,562,308 A | 2/1971 | Costa et al. |
| 5,721,014 A | 2/1998 | Fakler et al. |
| 6,020,511 A | 2/2000 | Vaartstra et al. |
| 6,475,276 B1 | 11/2002 | Elers et al. |
| 6,786,936 B2 | 9/2004 | Vaartstra |
| 7,632,351 B2 | 12/2009 | Thompson |

(Continued)

FOREIGN PATENT DOCUMENTS

| | | | |
|---|---|---|---|
| KR | 1020100061183 | * | 6/2010 |
| WO | 2012027357 A2 | | 3/2012 |

(Continued)

OTHER PUBLICATIONS

Anonymous author IP.com Prior Art Jul. 2005.*

(Continued)

*Primary Examiner* — Joseph Miller, Jr.
(74) *Attorney, Agent, or Firm* — Brooks Kushman P.C.

(57) ABSTRACT

A method of forming a thin film on a substrate which includes a step of contacting a surface with a precursor compound having a transition metal and one or more alkyl-1,3-diazabutadiene ligands is provided. The resulting modified surface is then contacted with an activating compound.

18 Claims, 15 Drawing Sheets

(56) References Cited

U.S. PATENT DOCUMENTS

| | | |
|---|---|---|
| 2001/0009695 A1 | 7/2001 | Saanila et al. |
| 2002/0013487 A1 | 1/2002 | Norman et al. |
| 2002/0098346 A1 | 7/2002 | Yitzchaik |
| 2005/0097991 A1 | 5/2005 | Sanjurjo et al. |
| 2005/0186342 A1* | 8/2005 | Sager et al. ............... 427/248.1 |
| 2006/0134331 A1 | 6/2006 | Thompson |
| 2006/0157863 A1 | 7/2006 | Marsh |
| 2007/0190248 A1 | 8/2007 | Elers et al. |
| 2009/0114874 A1 | 5/2009 | Norman et al. |
| 2009/0208637 A1 | 8/2009 | Chen et al. |
| 2010/0104755 A1 | 4/2010 | Dussarrat et al. |
| 2010/0181566 A1 | 7/2010 | Lee |
| 2012/0058270 A1 | 3/2012 | Winter et al. |
| 2012/0231579 A1 | 9/2012 | Quick et al. |
| 2013/0115768 A1 | 5/2013 | Pore et al. |
| 2013/0251903 A1 | 9/2013 | Han |

FOREIGN PATENT DOCUMENTS

| | | |
|---|---|---|
| WO | 2012/067439 A2 | 5/2012 |
| WO | 2012/176989 A1 | 12/2012 |

OTHER PUBLICATIONS

Shin, KR1020100061183, Jun. 2010, Eng machine translation.*
Knisley Organometallics 2011 v20 p5010-17.*
International Search Report for PCT/US2011/048792, Completed by the Korean Patent Office on Feb. 23, 2012, 3 Pages.
Rijnberg et al. Inorg. Chem. 1998, vol. 37, p. 56-63, "A Homologous Series of Homoleptic Zinc Bis(1,4-di-tert-butyl-1,4-diaza-1,3-butadiene) Complexes: Kx(Zn(t-BuNCHCHN-t-Bu)2), Zn(t-BuNCHCHN-t-Bu)2 and (Zn(t-BuNCHCHN-t-Bu)2)(Otf)x (x = 1, 2)."
Vidjayacoumar et al. Chem Mater. 2010, vol. 22, p. 4844-4853, "Investigation of AlMe3, BEt3, and ZnEt2 as Co-Reagents for Low-Temperature Copper Metal ALD/Pulsed-CVD."
Bart, S.C. et al., "Low-Valent α-Diimine Iron Complexes for Catalytic Olefin Hydrogenation," Organometallics 2005, v. 24, pp. 5518-5527.
d'Alnoncourt, R.N. et al., "The preparation of Cu/Al2O3 catalysts via CVD in a fluidized-bed reactor," Surface and Coatings Technology 201, pp. 9035-9904, 2007.
Dieck, H.T. et al., "Reaktionen von Bis(dizadien)eisen(O)," Komplexen. Chem. Ber., 120, pp. 1943-1950, Oct. 2002 (English Abstract).
Gardiner, M.G. et al., "Paramagnetic Bis(1,4-di-tert-butyl-1,4-diazabutadiene) Adducts of Lithium, Magnesium, and Zinc," Inorg. Chem. 1994, 33, pp. 2456-2461.
Ghosh, M. et al., "(α-Diimine)chromium Complexes: Molecular and Electronic Structures; a Combined Experimental and Density Functional Theoretical Study," Inorganic Chem., v. 47, n. 13, (2008), pp. 5963-5970.
Ghosh, M. et al., "A structural, spectroscopic and computational study of the molecular and electronic structure of a [bis(α-diiminato)magnese(II)] Π radical complex," Dalton Trans., 2008, pp. 5149-5151.
Gong, Y. et al., "The intra-annular acylamide chelate-coordinated compound: The keto-tautomer of metal (II)-milrione complex," J. of Molecular Structure 875 (2008), pp. 113-120.
Hassaan, "Mixed ligand complexes of bis(s-methyl-n-arylidene hydrazine carbodithioate) nickel (ii) chelates with some amino acids and nitrogenous heterocycles," J. of Islamic Academy [online] retrieved from http://www.medicaljournal-las.org/3_4Hassan.pdf on Jul. 1, 2010, pp. 269-272.
International Search Report dated Jul. 1, 2010 from corresponding PCT/US2010/035080 filed May 17, 2010, 2 pgs.
International Search Report for PCT/US2011/048792, Completed by the Korean Patent Office on Feb. 23, 2012, 3 pp.
International Search Report dated Aug. 17, 2012 from corresponding PCT/US12/040892 filed Jun. 5, 2012, pgs.
Kaltsoyannis, N., "Covalency in metal complexes of 1,4-diazabutadiene (dab). A density functional investigation of the electronic structures of [M(dab)2] (M = Li, Ga or Co) and [Th(NH3)NH2)3(dab)]," J. Chem. Soc., Dalton Trans., 1996, pp. 1583-1589.
Kalutarage, L.C. et al., "Low-Temperature Atomic Layer Deposition of Copper Films Using Borane Dimethylamine as the Reducing Co-reagent," Chem. Mater. 2014, 26, pp. 3731-3738.
Kalutarage, L.C. et al., "Synthesis, Structure, and Solution Reduction Reactions of Volatile and Thermally Stable Mid to Late First Row Transition Metal Complexes Containing Hydrazonate Ligands," Inorg. Chem. 2013, v. 52, pp. 5385-5394.
Kalutarage, L.C. et al., "Volatile and Thermally Stable Mid to Late Transition Metal Complexes Containing α-Imino Alkoxide Ligands, a New Strongly Reducing Coreagent, and Thermal Atomic Layer Deposition of Ni, Co, Fe, and Cr Metal Films," J. Am. Chem. Soc. 2013, 135, pp. 12588-12591.
Karunarathne, M.C. et al., "Exceptional thermal stability and high volatility in mid to late first row transition metal complexes containing carboyhydrazide ligands," Polyhedron 52 (2013), pp. 820-080.
Khusniyarov, M. M. et al., "Reversible Electron Transfer Coupled to Spin Crossover in an Iron Coordination Salt in the Solid State," Angew. Chem. Int. Ed. 2008, 47, pp. 1228-1231.
Khusniyarov, M.M. et al., "Molecular and Electronic Structures of Homoleptic Nickel and Cobalt Complexes with Non-Innocent Bulky Diimine Ligands Derived from Fluorinated 1,4-Diaza-1,3-butadiene (DAD) and Bis(arylimino) acenaphthene (BIAN)," Eur. J. Inorg. Chem. 2006, pp. 2985-2996.
Khusniyarov, M.M. et al., "Tuning the Oxidation Level, the Spin State, and the Degree of Electron Delocalization in Horn- and Heteroleptic Bis(α-diimine)iron Complexes," J. Am. Chem. Soc. 2009, v. 131, pp. 1208-1221.
Knisley, T.J. et al., "Low Temperature Growth of High Purity, Low Resistivity Copper Films by Atomic Layer Deposition," Chem. Mater. 2011, v. 23, pp. 4417-4419.
Knisley, T.J. et al., "Volatility and High Thermal Stability in Mid- to Late-First-Row Transition-Metal Dizazdienyl Complexes," Organometallics 2011, v. 30, pp. 5010-5017.
Kreisel, K.A. et al., "Synthesis, Characterization, and Electronic Structure of Diimine Complexes of Chromium,"Inorganic Chem., v. 74, n. 12, (2008), pp. 5293-5303.
Kreisel, K.A. et al., "The Shortest Metal-Metal Bond Yet: Molecular and Electronic Structure of a Dinuclear Chromium Diazadiene Complex," J. Am. Chem. Soc. 2007, v. 129, pp. 14162-14163.
Lim, B.S. et al., "Atomic layer deposition of transition metals," Nature Materials, v. 2, Nov. 2003, pp. 749-754.
Mac-Leod-Carey, D.A. et al., "Bix[2-(2,4-dioxopentan-3-ylidene-κO)-1-(4-methoxy-phenyphydrazinato-κN1] copper(II)," Acta Cryst. 2007, E63, pp. m670-m672.
Marten, J. et al., "3-(Arylhydrazono)pentane-2,4-diones and their Complexes with Copper(II) and Nickel(II)—Synthesis and Crystal Structures," Z. Anorg. Allg. Chem. 2005, v. 631, pp. 869-877.
Muresan, N. et al., "Bis(α-diimine)iron Complexes: Electronic Structure Determination by Spectroscopy and Broken Symmetry Density Functional Theoretical Calculations," Inorganic Chem., v. 47, n. 11, (2008), pp. 4579-4590.
Muresan, N. et al., "Bis(α-diimine)nickel Complexes: Molecular and Electronic Structure of Three Members of the Electron-Transfer Series [Ni(L)2]z (z=0, 1+, 2+) (L=2-Phenyl-1,4-bis(isopropyl)-1,4-diazabutadiene). A Combined Experimental and Theoretical Study," Inorganic Chem., v. 46, n. 13, (2007) pp. 5327-5337.
Muresan, N. et al., "Neutral (bis(1,4-diaza-1,3-butadiene)nickel complexes and their corresponding monocations: molecular and electronic structures. A combined experimental and density functional theoretical study," Dalton Trans., 2007, pp. 4390-4398.
Nassimbeni, L. et al., "The Crystal and Molecular Structure of the Bis-(5-ethyl-5-isoamylbarbiturato)bis(imidazole) Complex of Nickel(II)," Acta Cryst. (1974), B30, p. 2593-2602.
Pangani et al., "Coordination compounds of lanthanides with acetylhydrazine," Inorganica Chimca Acta, v. 94, issues 1-3, Feb. 1984, Abstract p. 79.
Pettinari, C. et al, "Copper and silver derivatives of scorpionates and related ligands," Polyhedron 23 (2004), pp. 451-469.

(56) References Cited

OTHER PUBLICATIONS

Popoff, N. et al., "Shifting from Ziegler-Natta to Phillips-Type Catalyst? A Simple and Safe Access to Reduced Titanium Systems for Ethylene Polymerization," Macromol. Rapid Commun. 2011, 32, pp. 1921-1924.

Rijnberg et al., "A Homologous Series of Homoleptic Zinc Bis(1,4-di-tert-butyl-1,4-diaza-1,3-butadiene) Complexes: Kx(Zn(t-BuNCHCHN-t-Bu)2 and (Zn(t-BuNCHCHN-t-Bu)2))(Otf)x (x=1,2)," Inorg. Chem. 1998, v. 37, pp. 56-63.

Robinson, M.A. et al., "Complexes Derived from Strong Field Ligands. XVII. Electronic Spectra of Octahedral Nickel(II) Complexes with Ligands of the α-Diimine and Closely Related Classes," Inorganic Chem., v. 2, n. 6, (1963), pp. 1178-1181.

Saito, T. et al., "1,4-Bis(trimethylsilyl)-,4-diaza-2,5-cyclohexadienes as Strong Salt-Free Reductants for Generating Low-Valent Early Transition Metals with Electron-Donating Ligands," J. Am. Chem. Soc. 2014, 136, pp. 5161-5170.

Svoboda, M. et al., "Bis(diazadien)metal(O)-Komplexe, III [1]1 Nickel(O)-bis(chelate) mit aliphatischen N-Substituenten," Z. Naturforsch. 86b, (1981), pp. 814-822—English Abstract.

Thompson, R.K. "Amidate Complexes of the Group 4 Metals," Synthesis, Reactivity, and Hydroamination Catalysis. Thesis, The University of British Columbia. http://hdl.handle.net/2429/1344. Available online Nov. 18, 2008, pp. 1-120

Tsurugi, H. et al., "Carbon Radical Generation by D0 Tantalum Complexes with α-Diimine Ligands through Ligand-Centered Redox Processes," J. Am. Chem. Soc. 2011, 133, pp. 18673-18683.

Tsurugi, H. et al., "Salt-Free Reducing Reagent of Bis(trimethylsilyl)cyclohexadiene Mediates Multielectron Reduction of Chloride Complexes of W(VI) and W(IV)," J. Am. Chem. Soc. 2013, 135, pp. 5986-5989.

Vidjayacoumar et al., "Investigation of AlMe3, BEt3, and ZnEt2 as Co-Reagents for Low Temperature Copper Metal ALD/Pulsed-CVD," Chem. Mater. 2010, v. 22, pp. 4844-4853.

Yilmaz, F. et al., "Bis-(5,5'-diethylbarbiturato) Copper(II) and Cadmium(II) Complexes with Ethylenediamine. Synthesis Crystal Structures, Spectroscopic and Thermal Characterization of cis-[Cu(barb)2(en] and {[Cd(barb)2(μ-en)]•2H2O)n," Z. Anorg. Allg. Chem. 2005, v. 631, pp. 1536-1540.

Non-Final Office Action mailed Apr. 7, 2014 in U.S. Appl. No. 13/319,793, filed Oct. 10, 2011, 7 pgs.

Non-Final Office Action mailed May 28, 2014 in U.S. Appl. No. 13/493,560, filed Jun. 11, 2012, 7 pgs.

Dieck H. et al., "Ruthenium Complexes with Diazadienes. 4.1 Arene Diazadiene Ruthenium (II) Complexes [(η6-Arene)(RN=CR'=NR)Ru(L)]n+(n=1, L= Cl, I, Alkyl; n = 2, L = MeCN, η2-C2H4) and Arene Diazadiene Ruthenium (0)," Organometallics 1986, 5, pp. 1449-1457.

Tromp, D.S. et al, "Synthesis of new (σ2-N,N'-diazadiene)(η2-alkene)platinum(0) compounds," Inorganica Chiica Acta 327 (2002), pp. 90-97.

Walther, D. et al., "Metal Complexes with 2,3-Bis(diphenylphosphino)-1,4-diazadiene Ligands: Synthesis, Structures, and an Intramolecular Metal-Mediated [4 + 2] Cycloaddition Employing a Benzene Ring as a Dienophile," Inorg. Chem., vol. 42, No. 2, 2003, pp. 625-632.

Final Office Action Mailed Sep. 24, 2014 in U.S. Appl. No. 13/493,560, filed Jun. 11, 2014, 23 pgs.

International Search Report, dated Oct. 27, 2014 in PCT/US2014/044669 filed Jun. 27, 2014, 3 pgs.

Non-Final Office Action mailed Jan. 14, 2015 in U.S. Appl. No. 13/930,471, filed Jun. 28, 2013, 7 pgs.

Elam, J.W. et al., "Nucleation and Growth of Noble Metals on Oxide Surfaces Using Atomic Layer Deposition," ECS Transactions, 3 (15) 2007, pp. 271-278.

Final Office Action mailed Jun. 8, 2015 in U.S. Appl. No. 14/318,501, filed Jun. 27, 2014, 11 pgs.

Non-final Office Action mailed Jan. 30, 2015 in U.S. Appl. No. 14/318,501, filed Jun. 27, 2014, 10 pgs.

\* cited by examiner

Table 2. Selected Bond Lengths (Å) and Angles (°) for 1.

| | |
|---|---|
| Cr1-N1 | 1.924(3) |
| Cr(1)-N(2) | 1.924(2) |
| Cr(1)-N(3) | 1.928(3) |
| Cr(1)-N(4) | 1.934(2) |
| Cr(1)-C(1) | 2.351(3) |
| Cr(1)-C(2) | 2.361(3) |
| C(1)-C(2) | 1.395(4) |
| C(11)-C(12) | 1.337(5) |
| C(1)-N(1) | 1.360(4) |
| C(2)-N(2) | 1.356(4) |
| C(11)-N(3) | 1.386(4) |
| C(12)-N(4) | 1.367(4) |
| N(1)-Cr(1)-N(2) | 91.79(11) |
| N(1)-Cr(1)-N(3) | 127.13(11) |
| N(1)-Cr(1)-N(4) | 118.60(11) |
| N(2)-Cr(1)-N(3) | 123.99(11) |
| N(2)-Cr(1)-N(4) | 114.94(11) |
| N(3)-Cr(1)-N(4) | 82.91(11) |
| Cr(1)-N(1)-C(1) | 89.69(19) |
| Cr(1)-N(2)-C(2) | 90.38(18) |
| Cr(1)-N(3)-C(11) | 112.1(2) |
| Cr(1)-N(4)-C(12) | 112.2(2) |

*Fig. 2*

Table 2. Selected Bond Lengths (Å) and Angles (°) for 1.

| Cr1-N1 | 1.924(3) |
|---|---|
| Cr(1)-N(2) | 1.924(2) |
| Cr(1)-N(3) | 1.928(3) |
| Cr(1)-N(4) | 1.934(2) |
| Cr(1)-C(1) | 2.351(3) |
| Cr(1)-C(2) | 2.361(3) |
| C(1)-C(2) | 1.395(4) |
| C(11)-C(12) | 1.337(5) |
| C(1)-N(1) | 1.360(4) |
| C(2)-N(2) | 1.356(4) |
| C(11)-N(3) | 1.386(4) |
| C(12)-N(4) | 1.367(4) |
| N(1)-Cr(1)-N(2) | 91.79(11) |
| N(1)-Cr(1)-N(3) | 127.13(11) |
| N(1)-Cr(1)-N(4) | 118.60(11) |
| N(2)-Cr(1)-N(3) | 123.99(11) |
| N(2)-Cr(1)-N(4) | 114.94(11) |
| N(3)-Cr(1)-N(4) | 82.91(11) |
| Cr(1)-N(1)-C(1) | 89.69(19) |
| Cr(1)-N(2)-C(2) | 90.38(18) |
| Cr(1)-N(3)-C(11) | 112.1(2) |
| Cr(1)-N(4)-C(12) | 112.2(2) |

*Fig. 3*

Table 3. Selected Bond Lengths (Å) and Angles (°) for 3-5.

| | 3 | 4 | 5 |
|---|---|---|---|
| M-N(1) | 1.952(1) | 1.929(1) | 1.919(1) |
| M-N(2) | 1.956(1) | 1.936(1) | 1.916(1) |
| M-N(3) | 1.953(1) | 1.931(1) | 1.917(1) |
| C(1)-C(2) | 1.393(2) | 1.393(2) | 1.401(2) |
| C(9)-C(9)' | 1.397(2) | 1.403(2) | 1.407(2) |
| C(1)-N(1) | 1.339(2) | 1.334(2) | 1.326(2) |
| C(2)-N(2) | 1.341(2) | 1.332(2) | 1.326(2) |
| C(9)-N(3) | 1.347(1) | 1.335(2) | 1.330(1) |
| N(1)-M-N(2) | 84.72(5) | 84.65(6) | 83.51(5) |
| N(1)-M-N(3) | 122.74(3) | 122.93(4) | 123.93(3) |
| N(2)-M-N(3) | 123.28(3) | 123.26(4) | 123.62(3) |
| N(3)-M-N(3)' | 85.00(5) | 84.77(6) | 83.65(5) |
| M-N(1)-C(1) | 110.18(10) | 110.76(11) | 112.33(10) |
| M-N(2)-C(2) | 109.97(9) | 110.61(11) | 112.61(10) |
| M-N(3)-C(9) | 110.07(6) | 110.87(8) | 112.55(7) |

*Fig. 4*

Table 4. Sublimation Temperature, Melting Point, Solid State Decomposition Temperature, Percent Recovery, and Percent Nonvolatile Residue for 1-5.

| Complex | Sublimation Temperature (°C/0.05 Torr) | Melting Point (°C) | Solid State Decomposition Temperature (°C) | % Recovery | % Nonvolatile Residue |
|---|---|---|---|---|---|
| 1 | 85 | 95 | 295 | 96.7 | 3.2 |
| 2 | 120 | 155-157 | 325 | 95.0 | 4.3 |
| 3 | 115 | 132-134 | 260 | 96.1 | 3.4 |
| 4 | 115 | 174-175 | 235 | 94.7 | 5.2 |
| 5 | 115 | 184-185 | 230 | 92.3 | 6.9 |

*Fig. 5*

THERMALLY STABLE VOLATILE PRECURSORS

CROSS-REFERENCE TO RELATED APPLICATION

This application claims the benefit of U.S. provisional application Ser. No. 61/376,495 filed Aug. 24, 2010, the disclosure of which is incorporated in its entirety by reference herein.

STATEMENT REGARDING FEDERALLY SPONSORED RESEARCH OR DEVELOPMENT

This invention was made with Government support under grant CHE0910475 awarded by the National Science Foundation. The Government has certain rights in the invention.

TECHNICAL FIELD

The present invention relates to thermally stable volatile compounds for depositing thin films by activated deposition processes, and, in particular, to thermally stable volatile compounds for depositing thin films by atomic layer deposition.

BACKGROUND

The growth of thin films is a central step in the fabrication of many functional materials and devices. While film growth efforts have been traditionally directed toward films with thicknesses greater than 100 nm, recent trends in several areas are calling for the growth of films ranging in thickness from a few atomic layers up to tens of nanometers.

As a significant example of this trend, the semiconductor industry has mandated a continuous reduction in microelectronics feature sizes from 65 nm in 2006 to 22 nm in 2012. This push toward smaller feature sizes requires controlled growth of films as thin as 1 nm. In addition to film growth on two-dimensional substrates such as etched silicon (Si) wafers, there is an increasing call to apply film growth techniques to nanoscale three-dimensional substrates such as nanoparticles, nanowires, carbon nanotubes, and biomaterials such as viruses, proteins, and natural fibers. Films on these substrates can play protective, passivating, or other functional roles, or may reproduce the shape of interesting nanoscale entities. The coatings may be as thin as a few monolayers to achieve the desired properties.

Atomic layer deposition ("ALD") is a thin film deposition technique that addresses many of the current technological demands. In a typical ALD process, a substrate is contacted with a first chemical composition that modifies the substrate for a first predetermined period of time (a pulse). Such modification involves adsorption to the surface of the substrate, reaction with the surface of the substrate, or a combination of adsorption and reaction. A purging gas is introduced to remove any lingering first gaseous chemical composition in the vicinity of the substrate. A second gaseous chemical composition that reacts with the modified substrate surface is introduced for a second predetermined period of time into the vicinity of the substrate to form a portion of the thin film. A purging gas is subsequently introduced to remove any lingering second chemical composition in the vicinity of the substrate. These steps of contacting the substrate with the first chemical composition, purging, contacting the substrate with the second gaseous chemical composition, and purging are usually repeated a plurality of times until a film of desired thickness is coated onto the substrate. Although the prior art ALD processes work well, there is unfortunately only a limited number of chemical precursors having the requisite thermal stability, reactivity, and vapor pressure for ALD.

Accordingly, there is a need for thermally stable volatile precursors suitable for depositing thin films by atomic layer deposition.

SUMMARY OF THE INVENTION

The present invention solves one or more problems of the prior art by providing, in at least one embodiment, a method for depositing a thin film on a surface of a substrate. The method includes a step of contacting the substrate with a vapor of a metal-containing compound described by any of formulae I to form a modified surface on the substrate:

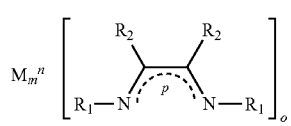

wherein:
M is a transition metal;
n is the formal charge of M;
m is an integer;
o is an integer such that the overall formal charge of the compound having formula I is 0;
p is the formal charge of the ligand within the brackets;
$R_1$ is $C_1$-$C_{12}$ alkyl, amine, or $C_6$-$C_{18}$ aryl; and
$R_2$ is hydrogen, $C_1$-$C_{10}$ alkyl, $C_6$-$C_{18}$ aryl, amino, $C_1$-$C_{12}$ alkylamino, or $C_2$-$C_{24}$ dialkylamino.

The modified surface is then contacted with a vapor of an activating compound to form at least a portion of the thin film on the surface of the substrate.

In another embodiment, a precursor compound useful for depositing a film on a substrate is provided. The precursor compound has formula I:

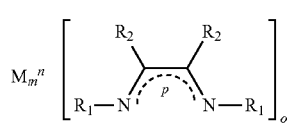

wherein:
M is a transition metal selected from groups 3-7;
n is the formal charge of M (typically, n is 0, 1+, 2+, or 3+);
p is the formal charge of the ligand within the brackets (typically, 0, 1−, or 2−)
m is an integer (typically, m is 1);
o is an integer such that the overall formal charge of the compound having formula I is 0 (typically, o is 1, 2, or 3);
$R_1$ is $C_1$-$C_{12}$ alkyl, amino, or $C_6$-$C_{18}$ aryl; and
$R_2$ is hydrogen, $C_1$-$C_{12}$ alkyl, $C_6$-$C_{18}$ aryl, amino, $C_1$-$C_{10}$ alkylamino, or $C_2$-$C_{24}$ dialkylamino.

BRIEF DESCRIPTION OF THE DRAWINGS

Exemplary embodiments of the present invention will become more fully understood from the detailed description and the accompanying drawings, wherein:

FIG. 2 is Table 1 which provides crystal data and data collection parameters for compounds 1 and 3-5;

FIG. 3 is Table 2 which provides selected bond lengths (Å) and angles (°) for 1;

FIG. 4 is Table 3 which provides selected bond lengths (Å) and angles (°) for compounds 3-5;

FIG. 5 is Table 4 which provides sublimation temperature, melting point, solid state decomposition temperature, percent recovery, and percent nonvolatile residue for compounds 1-5.

DETAILED DESCRIPTION OF EXEMPLARY EMBODIMENTS

Figure 1:
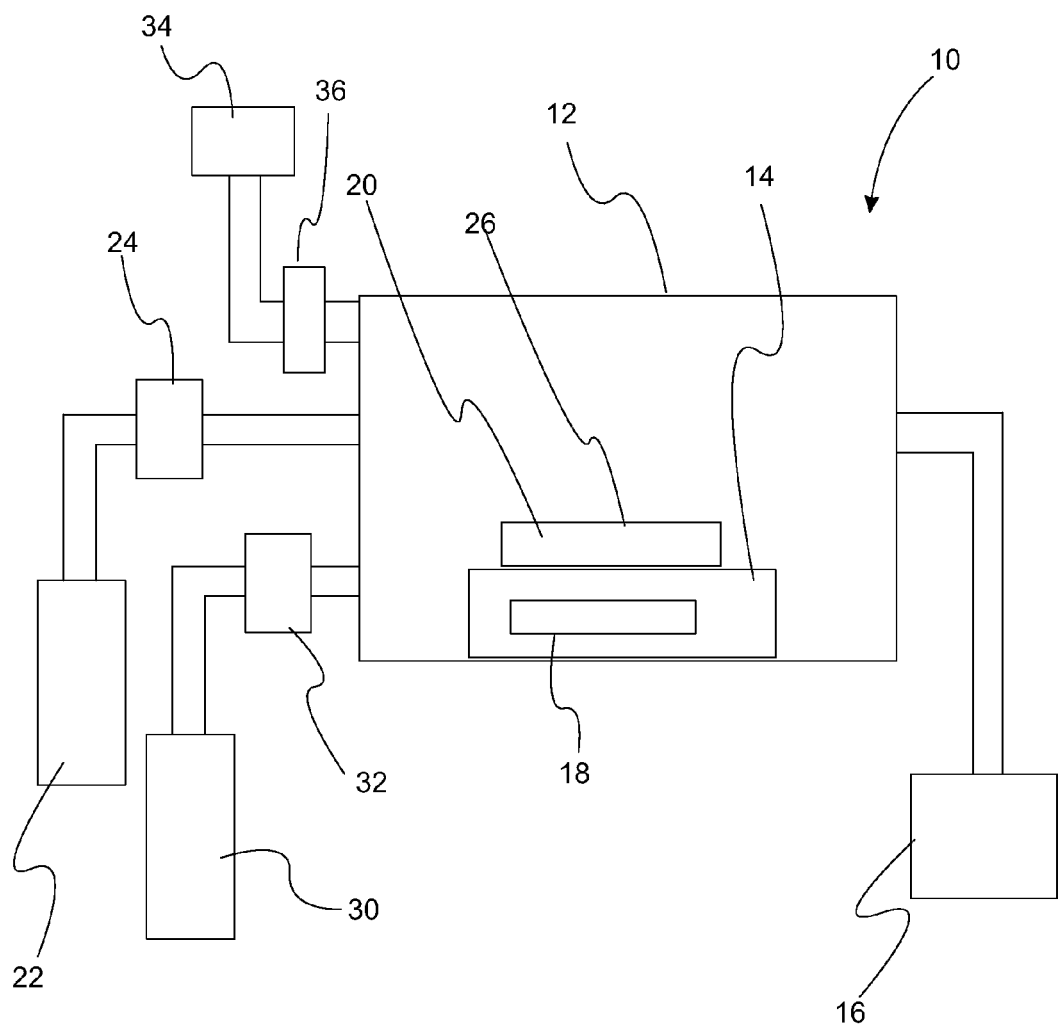
FIG. 1 is a schematic illustration of an atomic layer deposition system.
Figure 6:
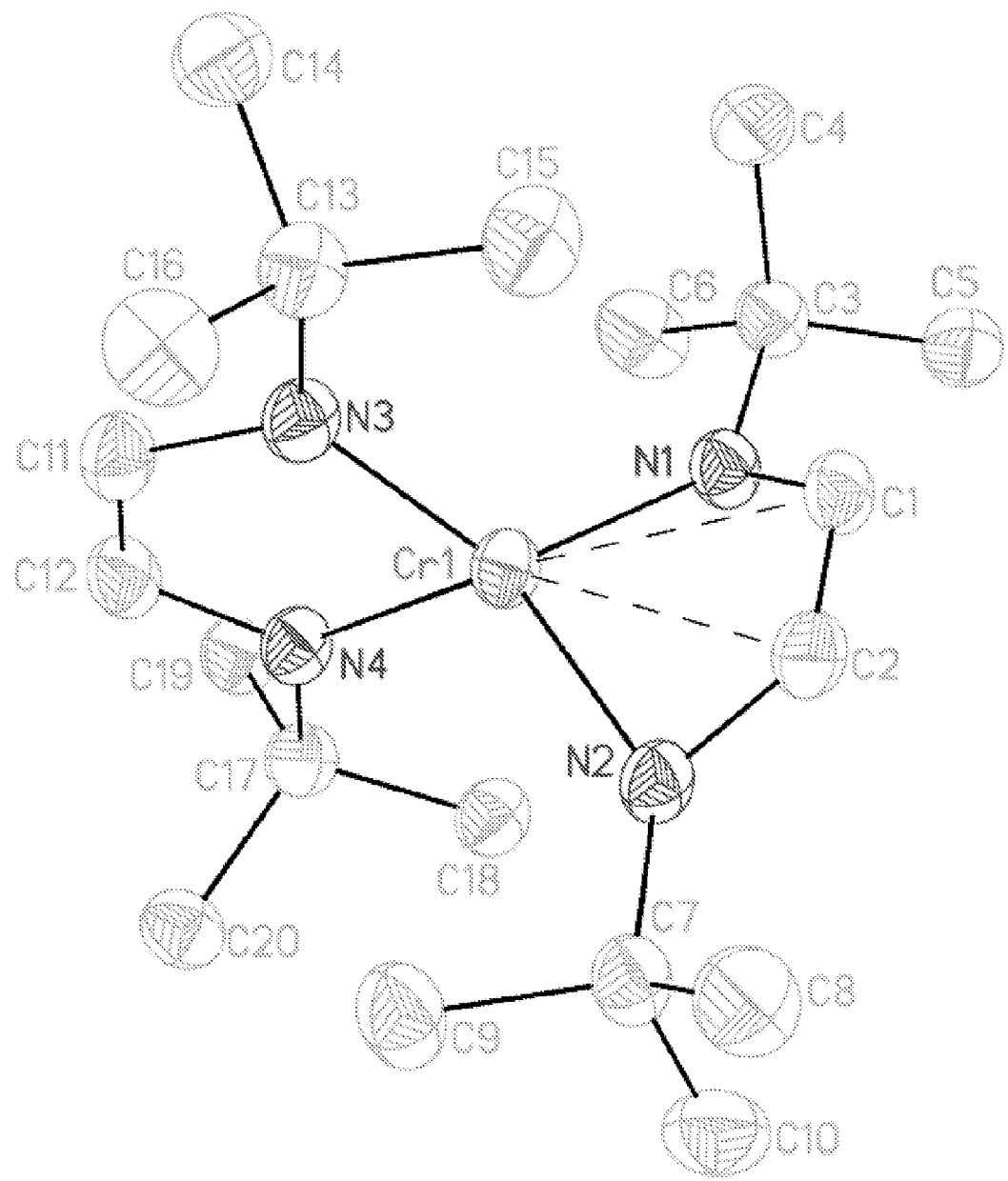
FIG. 6 provides a crystal structure of a perspective view of compound 1 with thermal ellipsoids at the 50% probability level.
Figure 7:
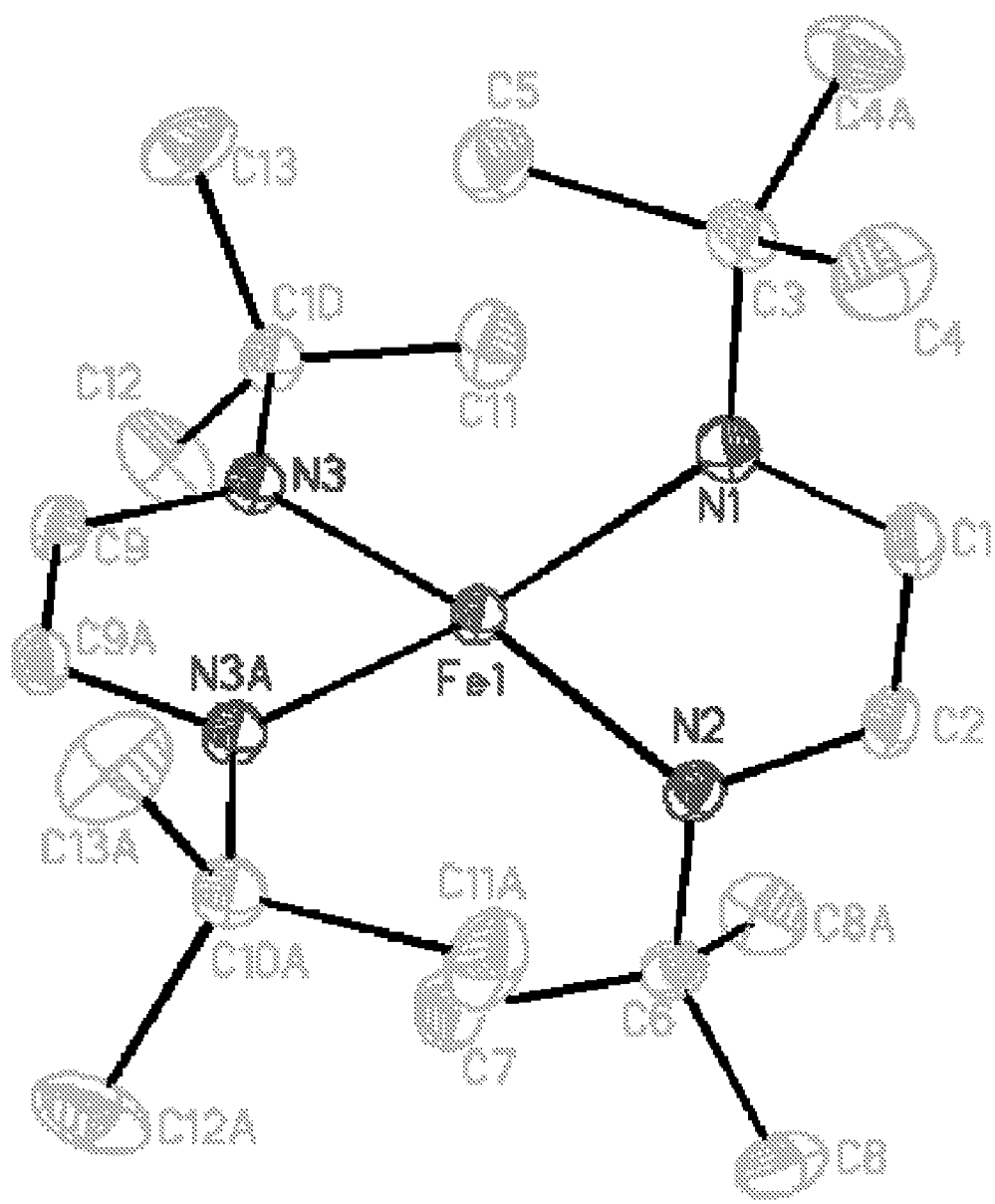
FIG. 7 provides a crystal structure of a perspective view of compound 3 with thermal ellipsoids at the 50% probability level.
Figure 8:
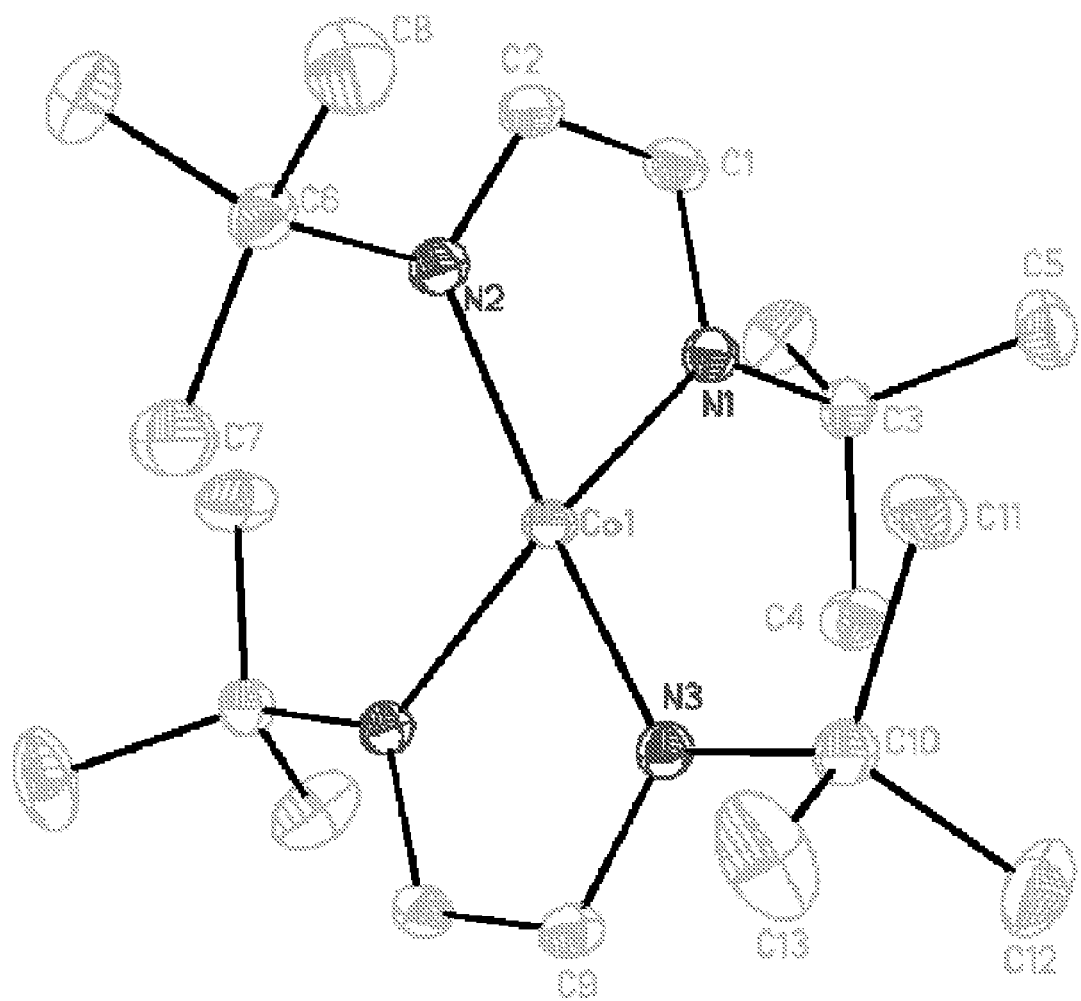
FIG. 8 provides a crystal structure of a perspective view of compound 4 with thermal ellipsoids at the 50% probability level.
Figure 9:
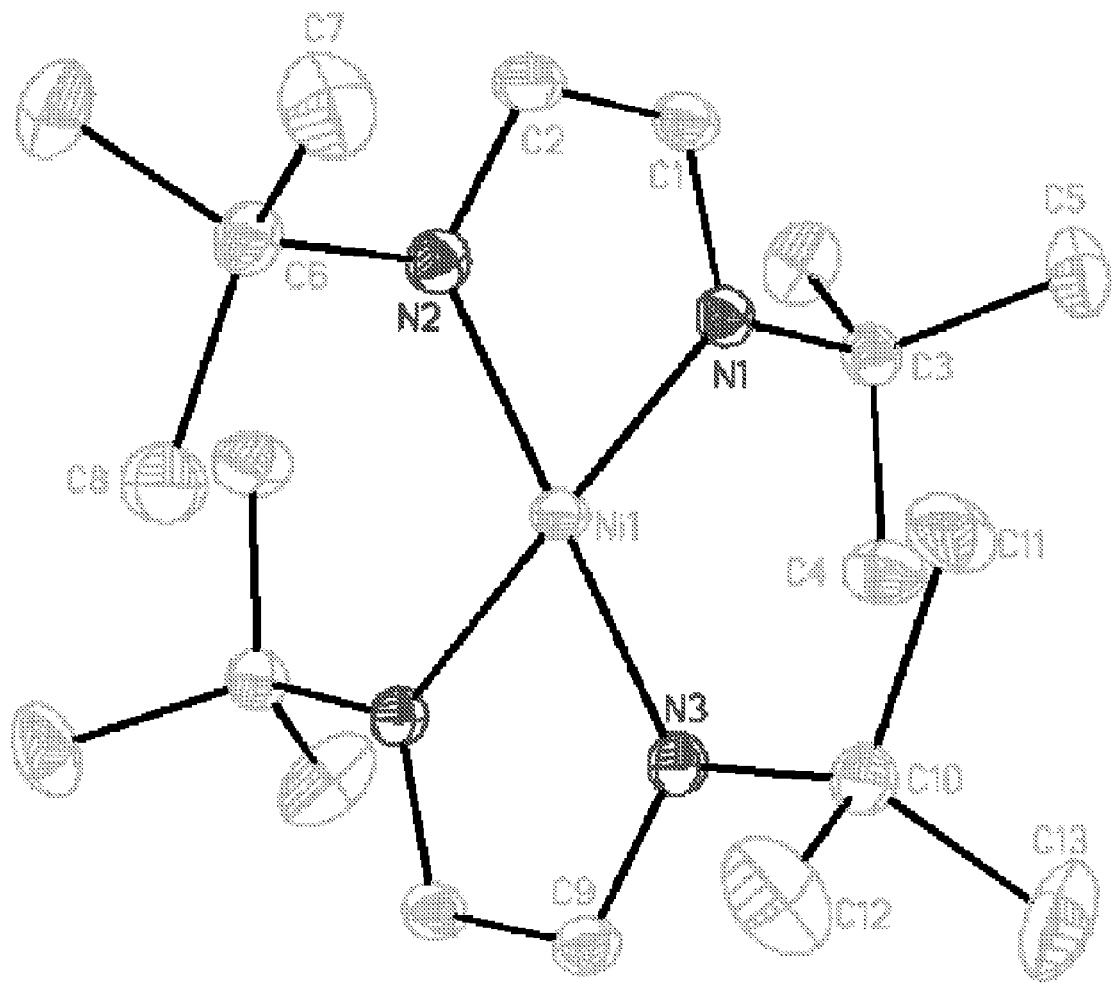
FIG. 9 provides a crystal structure of a perspective view of compound 5 with thermal ellipsoids at the 50% probability level.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The term "transition metal" as used herein means an element whose atom has an incomplete d sub-shell, or which can give rise to cations with an incomplete d sub-shell.

The term "thin film" as used herein means a coating on a substrate having a thickness less than about 0.5 microns. Typically, a thin film as used herein is a coating with a thickness less than about 500 nm. However, for many applications, a thin film as deposited by ALD is less than about 100 nm.

The term "thick film" as used herein means a coating on a substrate having a thickness greater than about 0.5 microns. Typically, a thick film is deposited by a chemical vapor deposition process (CVD).

In an embodiment of the present embodiment, a method for depositing a thin film on a surface of a substrate using the precursor compounds set forth above is provided. With reference to FIG. 1, deposition system 10 includes reaction chamber 12, substrate holder 14, and vacuum pump 16. Typically, the substrate is heated via heater 18. Virtually any substrate may be coated as is well known by one skilled in the art of ALD. Examples of substrates include, but are not limited to, silicon wafers, quartz plates, glass plates, and the like. The method has a deposition cycle comprising contacting substrate 20 with a vapor of a metal-containing compound described by any of formulae I, I', and II. The complex having formula I is described as follows:

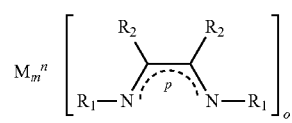

wherein:
M is a transition metal;
n is the formal charge of M (typically, n is 0, 1+, 2+, or 3+);
p is the formal charge of the ligand within the brackets (typically, 0, 1−, or 2−)
m is an integer (typically, m is 1);

o is an integer such that the overall formal charge of the compound having formula I is 0 (typically, o is 1, 2, or 3);

$R_1$ is $C_1$-$C_{12}$ alkyl, amine, or $C_6$-$C_{18}$ aryl; and $R_2$ is hydrogen, $C_1$-$C_{10}$ alkyl, $C_6$-$C_{18}$ aryl, amino, $C_1$-$C_{12}$ alkylamino, or $C_2$-$C_{24}$ dialkylamino.

The complex having formula I' is described as follows:

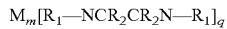

$$M_m[R_1-NCR_2CR_2N-R_1]_q \qquad \text{I'}$$

wherein

M is a transition metal;

m is an integer (typically, m is 1);

q is an integer (typically, q is 1, 2, or 3);

$R_1$ is $C_1$-$C_{12}$ alkyl, amino (i.e., —$NH_2$), or $C_6$-$C_{18}$ aryl; and $R_2$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino.

The complex having formula II is described as follows:

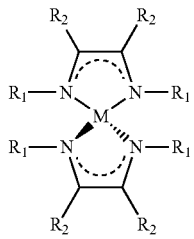

wherein

M is a transition metal;

$R_1$ is $C_1$-$C_{12}$ alkyl, amino (i.e., —$NH_2$), or $C_6$-$C_{18}$ aryl; and $R_2$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino.

In a refinement, the compounds having formulae I, I', and II are activated via a plasma prior to contacting the substrate. In particular, the vapor is introduced from precursor source 22 into reaction chamber 12 for a predetermined pulse time. The pulse time is controlled via control valve 24. At least a portion of the vapor of the metal-containing compound modifies (e.g, adsorbs or reacts with) substrate surface 26 to form a modified surface. The method further comprises contacting the modified surface with a vapor of an activating compound from activating compound source 30 for a predetermined pulse time. The pulse time is controlled via control valve 32. The activating compound causes the metal-containing compound to react and form at least a portion of the thin film on the surface of the substrate. The reduced pressure of chamber 12 is maintained by vacuum pump 16.

In a variation of the present embodiment, the method further comprises removing at least a portion of the vapor of the metal containing compound that is lingering in the gas phase (i.e., has not adsorbed or reacted with the substrate) from the vicinity of the substrate before introducing the vapor of the activating compound and removing at least a portion of the vapor of the activating compound from the vicinity of the substrate. The metal-containing compound and the activating compound are removed in purging steps by introducing a purge gas from purge source 34 into reaction chamber 12 for a predetermined purge time. The purge time is controlled by control valve 36.

In another variation, the method further includes at least one additional deposition cycle comprising sequentially contacting the substrate with the vapor of a metal-containing compound (formulae I, I', and II) and then the vapor of an activating compound. In some refinements, the substrate is contacted for a plurality of additional deposition cycles. For example, the substrate may be contacted with from 1 to several thousand deposition cycles depending on the thickness of the film desired.

In another variation, the activating compound is a reducing agent. In this variation, the resulting thin film is a metallic film. Examples of useful reducing agents include, but are not limited to, molecular hydrogen, atomic hydrogen, silane, disilane, organosilanes, compounds containing Si—H bonds, germane, organogermanes, compounds containing Ge—H bonds, stannane, compounds containing Sn—H bonds, other metal hydride compounds, formic acid, glyoxalic acid, oxalic acid, other carboxylic acids, diborane, compounds containing B—H bonds, hydrazine, carbon-substituted hydrazines, formalin, formaldehyde, organic alcohols, organoaluminum compounds, organozinc compounds, other organometallic compounds, plasma-activated versions of the above compounds.

In still another variation, the activating compound is an oxidizing agent with the resulting thin film being a metal oxide. Examples of useful oxidizing agents include, but are not limited to, water, ozone, molecular oxygen, atomic oxygen, organic alcohols, hydrogen peroxide, organic hydroperoxides, organic peroxides, nitrous oxide, plasma-activated versions of the above compounds.

In still another variation, the activating compound is a nitrogen-containing agent with the resulting thin film being a metal nitride. Examples of such nitrogen activating compounds include, but are not limited to, ammonia, hydrazine, alkyl-substituted hydrazines, and plasma activated versions thereof.

During film formation by the method of the present embodiment, the substrate temperature will be at a temperature suitable to the properties of the chemical precursor(s) and film to be formed. In a refinement of the method, the substrate is set to a temperature from about 0 to 1000° C. In another refinement of the method, the substrate has a temperature from about 50 to 450° C. In another refinement of the method, the substrate has a temperature from about 100 to 250° C. In still another refinement of the method, the substrate has a temperature from about 150 to 400° C. In another refinement of the method, the substrate has a temperature from about 200 to 300° C.

Similarly, the pressure during film formation is set at a value suitable to the properties of the chemical precursors and film to be formed. In one refinement, the pressure is from about $10^{-6}$ Torr to about 760 Torr. In another refinement, the pressure is from about 0.1 millitorr to about 10 Torr. In still another refinement, the pressure is from about 1 to about 100 millitorr. In yet another refinement, the pressure is from about 1 to 20 millitorr.

Pulse times and purge times also depend on the properties of the chemical precursors and the geometric shape of the substrates. Thin film growth on flat substrates uses short pulse and purge times, but pulse and purge times in ALD growth on 3-dimensional substrates can be very long. Therefore, in one refinement, pulse times and purge times are each independently from about 0.0001 to 200 seconds. In another refinement, pulse and purge times are each independently from about 0.1 to about 10 seconds.

As set forth above, $R_1$ is a $C_1$-$C_{12}$ alkyl or $C_6$-$C_{18}$ aryl. In a variation, $R_1$ is $C_1$-$C_4$ alkyl. Specific examples for $R_1$ include, but are not limited to, methyl, ethyl, propyl, n-butyl, sec-butyl, isobutyl, t-butyl, and the like. In a particularly useful refinement, $R_1$ is t-butyl. In another variation, $R_1$ is $C_6$-$C_{10}$ aryl. In this refinement, specific examples for $R_1$ include, but are not limited to, phenyl, biphenyl, napthyl, and the like. In a further refinement, it should be appreciated that the definitions for $R_1$ include substituted variations of such groups. Examples of substituents include, but are not limited to, halogen, hydroxyl, $-NO_2$, and in the case of aryl, $C_1$-$C_4$ alkyl. These substituents are particularly relevant when $R_1$ is aryl.

As set forth above, $R_2$ is a $C_1$-$C_{12}$ alkyl or $C_6$-$C_{18}$ aryl. In a variation, $R_2$ is $C_1$-$C_4$ alkyl. In this refinement, specific examples for $R_2$ include, but are not limited to, methyl, ethyl, propyl, n-butyl, sec-butyl, isobutyl, t-butyl, and the like. It should also be appreciated that when $R_2$ is $C_1$-$C_{12}$ alkylamino or $C_2$-$C_{22}$ dialkylamino, the alkyl component is the same as set forth for when $R_2$ is a $C_1$-$C_{12}$ alkyl. Therefore, additional specific examples for $R_2$ include, but are not limited to, methylamino, ethylamino, propylamino, diethylamino, dimethylamino, dipropylamino, and the like. In another refinement, $R_2$ is $C_6$-$C_{10}$ aryl. In this refinement, specific examples for $R_2$ include, but are not limited to, phenyl, biphenyl, napthyl, and the like. In a further refinement, it should be appreciated that the definitions for $R_2$ include substituted variations of such groups. Examples of substituents include, but are not limited to, halogen, hydroxyl, $-NO_2$, and in the case of aryl, $C_1$-$C_4$ alkyl. These substituents are particularly relevant when $R_2$ is aryl.

In another variation of the present embodiment, M is a metal in a 0, 1+, 2+, or 3+ oxidation state. Examples of useful transition metals for M include, but are not limited to, Cu, Ni, Co, Cr, Mn, Fe, W, Mo, Ti, Zr, Hf, Rf, V, Nb, Ta, Re, Ru, Rh, Ir, Pd, Pt, and Au. Particularly useful examples for M include, but are not limited to, Cr(II), Mn(II), Fe(II), Co(II), and Ni(II). In a refinement, M is a transition metal selected from groups 3-7 of the periodic table.

In another embodiment, a precursor compound for thin and/or thick film deposition, and, in particular, for deposition of a thin film is provided. The precursor compound has formula I:

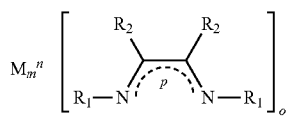

wherein:
M is a transition metal selected from groups 3-7 of the periodic table, Ru, Pd, Pt, Rh, and Ir;
n is the formal charge of M (typically, n is 0, 1+, 2+, or 3+);
p is the formal charge of the ligand within the brackets (typically, 0, 1−, or 2−)
m is an integer (typically, m is 1);
o is an integer such that the overall formal charge of the compound having formula I is 0 (typically, o is 1, 2, or 3);
$R_1$ is $C_1$-$C_{12}$ alkyl, amine, or $C_6$-$C_{18}$ aryl; and
$R_2$ is hydrogen, $C_1$-$C_{10}$ alkyl, $C_6$-$C_{18}$ aryl, amino, $C_1$-$C_{12}$ alkylamino, or $C_2$-$C_{24}$ dialkylamino.

Alternatively, the precursor compounds have formula I':

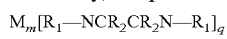

wherein
M is a transition metal selected from groups 3-7 of the periodic table, Ru, Pd, Pt, Rh, and Ir;
m is an integer (typically, m is 1);
q is an integer (typically, q is 1, 2, or 3);
$R_1$ is $C_1$-$C_{12}$ alkyl, amino (i.e., $-NH_2$), or $C_6$-$C_{18}$ aryl; and
$R_2$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino.

As set forth above, $R_1$ is a $C_1$-$C_{12}$ alkyl or $C_6$-$C_{18}$ aryl. In a variation, $R_1$ is $C_1$-$C_4$ alkyl. Specific examples for $R_1$ include, but are not limited to, methyl, ethyl, propyl, n-butyl, sec-butyl, isobutyl, t-butyl, and the like. In a particularly useful refinement, $R_1$ is t-butyl. In another variation, $R_1$ is $C_6$-$C_{10}$ aryl. In this refinement, specific examples for $R_1$ include, but are not limited to, phenyl, biphenyl, napthyl, and the like. In a further refinement, it should be appreciated that the definitions for $R_1$ include substituted variations of such groups. Examples of substituents include, but are not limited to, halogen, hydroxyl, $-NO_2$, and in the case of aryl, $C_1$-$C_4$ alkyl. These substituents are particularly relevant when $R_1$ is aryl.

As set forth above, $R_2$ is a $C_1$-$C_{12}$ alkyl or $C_6$-$C_{18}$ aryl. In a variation, $R_2$ is $C_1$-$C_4$ alkyl. In this refinement, specific examples for $R_2$ include, but are not limited to, methyl, ethyl, propyl, n-butyl, sec-butyl, isobutyl, t-butyl, and the like. It should also be appreciated that when $R_2$ is $C_1$-$C_{12}$ alkylamino or $C_2$-$C_{22}$ dialkylamino, the alkyl component is the same as set forth for when $R_2$ is a $C_1$-$C_{12}$ alkyl. Therefore, additional specific examples for $R_2$ include, but are not limited to, methylamino, ethylamino, propylamino, diethylamino, dimethylamino, dipropylamino, and the like. In another refinement, $R_2$ is $C_6$-$C_{10}$ aryl. In this refinement, specific examples for $R_2$ include, but are not limited to, phenyl, biphenyl, napthyl, and the like. In a further refinement, it should be appreciated that the definitions for $R_2$ include substituted variations of such groups. Examples of substituents include, but are not limited to, halogen, hydroxyl, $-NO_2$, and in the case of aryl, $C_1$-$C_4$ alkyl. These substituents are particularly relevant when $R_2$ is aryl.

In another variation of the present embodiment, M is a metal in a 0, 1+, 2+, or 3+ oxidation state. Examples of useful transition metals for M, include but are not limited to, Cu, Ni, Co, Cr, Mn, Fe, W, Mo, Ti, Zr, Hf, Rf, V, Nb, Ta, Re, Ru, Rh, Ir, Pd, Pt, and Au. Particularly useful examples for M include, but are not limited to, Cr(II), Mn(II), Fe(II), Co(II), and Ni(II).

In another variation of the present embodiment, a precursor compound having formula II is provided:

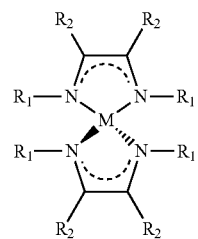

wherein
M is a transition metal selected from groups 3-7 of the periodic table, Ru, Pd, Pt, Rh, and Ir;
$R_1$ is $C_1$-$C_{12}$ alkyl, amino (i.e., $-NH_2$), or $C_6$-$C_{18}$ aryl; and
$R_2$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino.

The compounds set forth above are found to possess a number of useful properties that are relevant to thin and thick film deposition processes. For example, many of these compounds sublime at temperatures from 80 to 120° C. at reduced pressures (e.g., about 1 Torr). The compounds of the present embodiment tend to decompose at high temperatures with minimal residues being formed. Many of the compounds of the present invention decompose to form metal foils.

The following examples illustrate the various embodiments of the present invention. Those skilled in the art will recognize many variations that are within the spirit of the present invention and scope of the claims.

Results and Discussion

Synthesic Aspects.

Treatment of anhydrous metal(II) chlorides ($MCl_2$, M=Cr, Mn, Fe, Co, Ni) with two equivalents of 1,4-di-tert-butyl-diaza-1,3-butadiene and two equivalents of lithium metal afforded complexes of the formula $M(^{tBu2}DAD)_2$ (DAD=diazobutadiene) as purple (1), black (2), brown (3), blue (4), and dichroic red/green (5) crystalline powders (eq 1). Crystalline samples of 1-5 were subsequently obtained either by sublimation or crystallization in hexane at −23° C. The synthetic procedure is a modification of previous routes to transition metal complexes containing 1,4-diaza-1,3-butadiene ligands. It was not possible to prepare any copper(II) or copper(I) complexes containing $^{tBu2}DAD$ ligands, since all reactions afforded copper powders. The compositions of 1-5 were determined by a combination of analytical and spectroscopic techniques, and by X-ray crystal structure determinations of 1 and 3-5. Complex 5 is the only diamagnetic species in the series, and revealed tert-butyl and imino hydrogen atom resonances at δ 1.93 and 8.95, respectively, in the $^1H$ NMR spectrum in benzene-$d_6$. In the infrared spectra of 1-5, the carbon-nitrogen stretching frequencies were observed between 1716 and 1698 $cm^{-1}$. Solid state magnetic moments for 1-4 were 2.83, 3.85, 2.88, and 1.75 BM, respectively. Very similar values were measured in benzene solution using the Evans method, suggesting similar molecular structures in the solid state and solution. The magnetic moments for 1-4 are very close to those expected for high spin M(II) ions that are antiferromagnetically coupled to two unpaired electrons of radical anion $^{tBu2}DAD$ ligands (Chart 1, form B). Analogous magnetic coupling is well established in transition metal complexes containing 1,4-diaza-1,3-butadiene radical anion ligands with various alkyl and aryl substituents. Complexes 3 and 5 have been previously reported, and 4 was studied theoretically. The solution state magnetic moment reported for 3 in benzene solution was 2.88 BM, which is very similar to the values of 2.88 and 2.68 BM that were observed herein for the solid state and benzene solution magnetic moments, respectively. The $^1H$ NMR spectrum previously reported for 5 exactly match that reported herein.

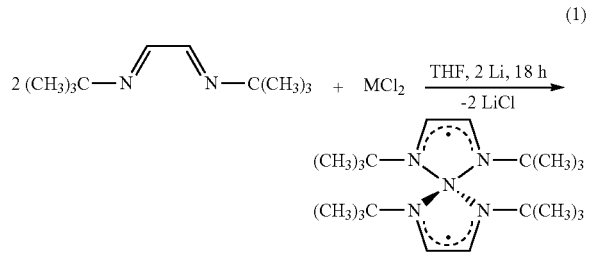

(1)

1, M = Cr, 38%
2, M = Mn, 81%
3, M = Fe, 47%
4, M = Co, 36%
5, M = Ni, 41%

X-Ray Crystal Structures of 1-5.

The X-ray crystal structures of 1 and 3-5 were determined to establish their solid-state configurations. Despite multiple attempts, high quality crystals of 2 could not be obtained, although a low resolution X-ray structure revealed a monomeric, tetrahedral complex with a molecular arrangement similar to those of 3-5. Experimental crystallographic data are summarized in Table 1 (FIG. 2), selected bond lengths and angles are given in Tables 2 (FIG. 3) and 3 (FIG. 4), and perspective views are presented in FIGS. 6-9.

Complexes 1 and 3-5 adopt mononuclear structures, with distorted tetrahedral geometry about the metal centers. In 3-5, the planes of the $C_2N_2$ ligand cores are constrained by symmetry to be orthogonal. Complex 1 crystallizes with two independent molecules in the unit cell; both molecules are identical within experimental uncertainty and only data for the molecule containing Cr(1) are presented herein. Complexes 3-5 are isostructural. Complex 5 was obtained in the space group Pnma. The metal-nitrogen bond lengths (1, 1.924 (2)-1.934(2) Å; 3, 1.952(1)-1.956(1) Å; 4, 1.929(1)-1.936(1) Å; 5, 1.916(1)-1.919 Å) fall into a narrow range. The metal-nitrogen bond distances in 1 are considerably shorter than those found in $Cr(2,6-iPr_2C_6H_3N=CHC(Me)=NC_6H_3-2,6-iPr_2)_2$ (2.019(1), 2.030(1) Å) and $Cr(2,6-iPr_2C_6H_3N=CHCH=NC_6H_3-2,6-iPr_2)_2$ (2.030(4), 2.035(5) Å), but are similar to the values observed in $Cr_2(2,6-iPr_2C_6H_3N=CHCH=NC_6H_3-2,6-iPr_2)_2$ (1.914(2), 1.913(2) Å). The metal-nitrogen bond distances in 3 are similar to those of $Fe(C_6F_5N=C(Me)C(Me)=NC_6F_5)_2$ (1.962(2), 1.962(2) Å), but are shorter than those found in $Fe(2,6-iPr_2C_6H_3N=C(Me)C(Me)=NC_6H_3-2,6-iPr_2)_2$ (1.988(9)-2.077(8) Å). $Fe(C_6F_5N=C(Me)C(Me)=NC_6F_5)_2$ is proposed to contain two diazadienyl radical anion ligands, based upon the carbon-carbon and carbon-nitrogen distances of the ligand core. By contrast, one of the ligand core carbon-carbon distances in $Fe(2,6-iPr_2C_6H_3N=C(Me)C(Me)=NC_6H_3-2,6-iPr_2)_2$ is about 0.08 Å longer than the other, suggesting more neutral character in one ligand (Chart 1, form C). The cobalt-nitrogen distances in 4 are similar to those of $Co(C_6F_5N=C(Me)C(Me)=NC_6F_5)_2$ (1.931(3), 1.932(3) Å). The nickel-nitrogen bond lengths in 5 compare well with those of $Ni(C_6F_5N=C(Me)C(Me)=NC_6F_5)_2$ (1.9173(18), 1.9165(17) Å) and $Ni(2,6-Me_2C_6H_3N=CHC(Me)=NC_6H_3-2,6-Me_2)_2$ (1.921(1)-1.948(1) Å), but are shorter than those found in $Ni(2,6-iPr_2C_6H_3N=CHC(Me)=NC_6H_3-2,6-iPr_2)_2$ (1.963(2)-1.999(2) Å). Interestingly, the X-ray crystal structure of a polymorph of 5 was reported, and has nickel nitrogen bond lengths of 1.906 to 1.941 Å, with an average value of 1.923 Å.

The average metal-nitrogen bond lengths follow the order 3 (1.954 Å)>4 (1.932 Å)>1 (1.928 Å)>5 (1.917 Å), even though the ionic radii of the metal ions decrease in the order Cr(II) (0.80 Å)>Fe(II) (0.78 Å)>Co(II) (0.745 Å)>Ni(II) (0.69 Å). Hence, the chromium-nitrogen distances in 1 are shorter than expected, based upon the ionic radius of the Cr(II) ion relative to those of the other ions. Closer inspection of 1 reveals that there are two types of $^{tBu2}DAD$ ligands. The ligand that contains N(1) and N(2) has the C(1) and C(2) atoms tilted toward the chromium atom, with chromium-carbon distances of 2.351(3) and 2.361(3) Å. By contrast, the ligand containing N(3) and N(4) forms a planar $CrN_2C_2$ ring and has chromium-carbon distances of 2.758 and 2.767 Å. For comparison, the metal-carbon distances associated with the $^{tBu2}DAD$ core carbon atoms of 3-5 range between 2.706 and 2.727 Å and the metal ions are coplanar with the $N_2C_2$ rings. The chromium-carbon interactions in the ligand in 1 containing C(1) and C(2) appear to reflect the additional empty d orbitals associated with the $d^4$ Cr(II) ion. The modified bonding to one of the ligands in 1 may alleviate interligand tert-butyl crowding by a small amount, thereby allowing slightly shorter chromium-nitrogen bond lengths than expected based upon the ionic radius of the Cr(II) ion.

It is well established that the carbon-carbon and carbon-nitrogen bond lengths within the $C_2N_2$ ligand cores offer a reliable tool for distinguishing among forms A, B, and C in Chart 1. In 3-5, the carbon-carbon and carbon-nitrogen bond lengths fall into the narrow ranges of 1.393 to 1.407 Å and 1.326 to 1.347 Å, respectively. These values are in between those expected for single and double bonds, and are diagnostic of the $^{tBu2}$DAD radical anion. These assignments are also consistent with the magnetic moment data described above. The situation with 1 is a little more complex, since one ligand has a carbon-carbon distance of 1.337(5) Å and carbon-nitrogen distances of 1.386(4) and 1.367(4) Å. The other ligand is bent toward the chromium ion and has a carbon-carbon distance of 1.395(4) Å and carbon-nitrogen distances of 1.360(4) and 1.356(4) Å. The bond distances of the latter ligand are very similar to those of 3-5, and support assignment as a $^{tBu2}$DAD radical anion. In the former ligand, only the carbon-carbon bond length differs significantly within experimental error from that of the latter ligand. Hence, there may be a slightly higher amount of charge localization on the nitrogen atoms in the former ligand, but any differences in the structural data are small and at the edge of experimental uncertainty. The magnetic moment data for 1 described above are consistent with the presence of two $^{tBu2}$DAD radical anion ligands that are antiferromagnetically coupled to a high spin $d^4$ Cr(II) ion. Complexes of the formula FeCl$_3$($^{tBu2}$DAD), CoCl$_2$($^{tBu2}$DAD) and NiBr$_2$($^{tBu2}$DAD) have been structurally characterized, and have $C_2N_2$ ligand core carbon-carbon and carbon-nitrogen distances of 1.455-1.510 and 1.247-1.275 Å, respectively. The carbon-carbon distances in these complexes are close to those expected for a single bond, and the carbon-nitrogen distances are close to those expected for a double bond. Hence, these ligands are consistent with neutral form C in Chart 1, and are distinct from the radical anion ligand type B observed in 1 and 3-5.

Volatility and Thermal Stability.

Figure 10:
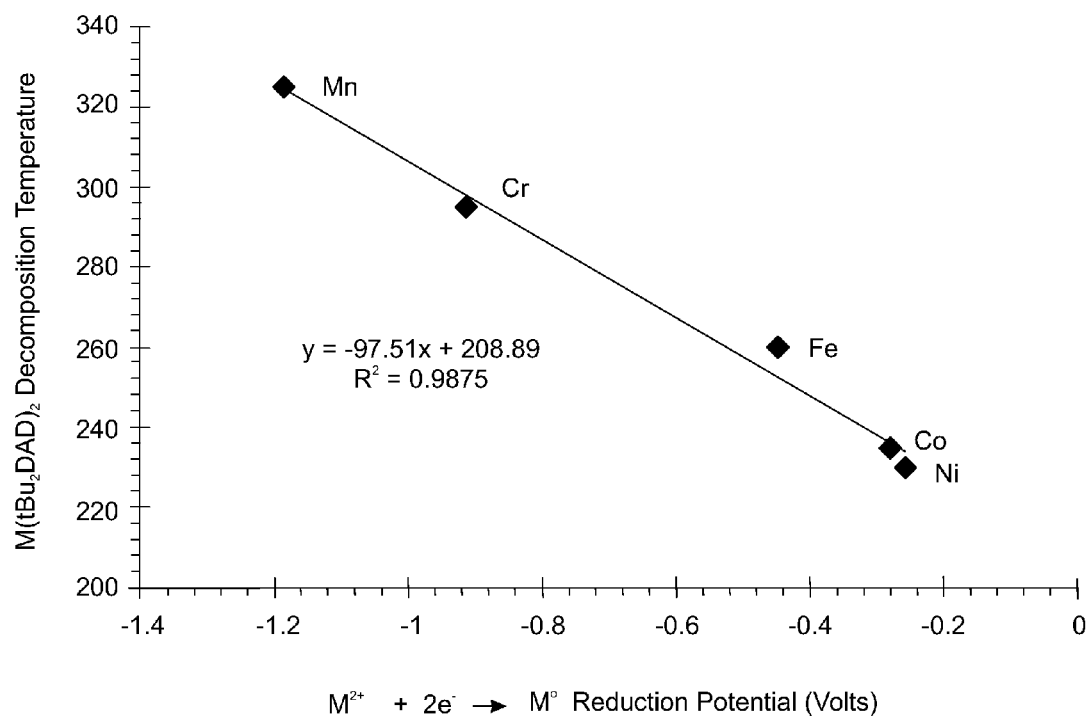
FIG. 10 provides a plot of the solid-state decomposition temperatures of compounds 1-5 versus the $M^{2+}/M^0$ redox couple.

The volatility and thermal stability of 1-5 were studied by preparative sublimation, thermogravimetric analyses, and melting point/solid state thermal decomposition experiments to assess their potential for use as ALD precursors. Sublimation data, melting points, and solid state decomposition temperatures for 1-5 are listed in Table 4 (FIG. 5). In preparative sublimations, 0.5-1.0 g samples were sublimed at 0.05 Torr and the temperature was adjusted so that the sublimation was complete in less than five hours. In previous work, we have established that these preparative sublimation temperatures approximate the temperatures required for the vapor phase delivery of precursors in our ALD reactors. Under these conditions, the sublimed recoveries of 1-5 were ≥92.3% with nonvolatile residues of ≤6.9%. The high air sensitivity of 1-5 limited the ability to obtain higher sublimed recoveries since product isolation had to be conducted in an inert atmosphere dry box. Additionally, exposure to trace amounts of air during sample loading may have led to higher nonvolatile residues. The solid state decomposition temperatures were determined visually by monitoring sealed glass capillary tubes containing a few milligrams of 1-5, and then noting the temperatures at which metal foils began to appear. These solid state decomposition temperatures are generally very close to the upper limit of self-limited ALD growth in plots of growth rate versus deposition temperature, and are thus very useful. The solid state decomposition temperature of 2 is the highest at 325° C., while that of 5 is the lowest at 230° C. Interestingly, a plot of the solid state decomposition temperatures of 1-5 versus the $M^{2+} \rightarrow M^0$ reduction potentials is linear (FIG. 10), suggesting that decomposition might occur through transfer of an electron from the $^{tBu2}$DAD radical anion ligands to the metal ions. The failure to produce copper(II) or copper(I) complexes noted above likely arises from immediate reduction of the copper ions to copper metal due to the large positive reduction potentials of these ions ($Cu^{2+}$ 0.342 V, $Cu^+$ 0.521 V).

Figure 11:
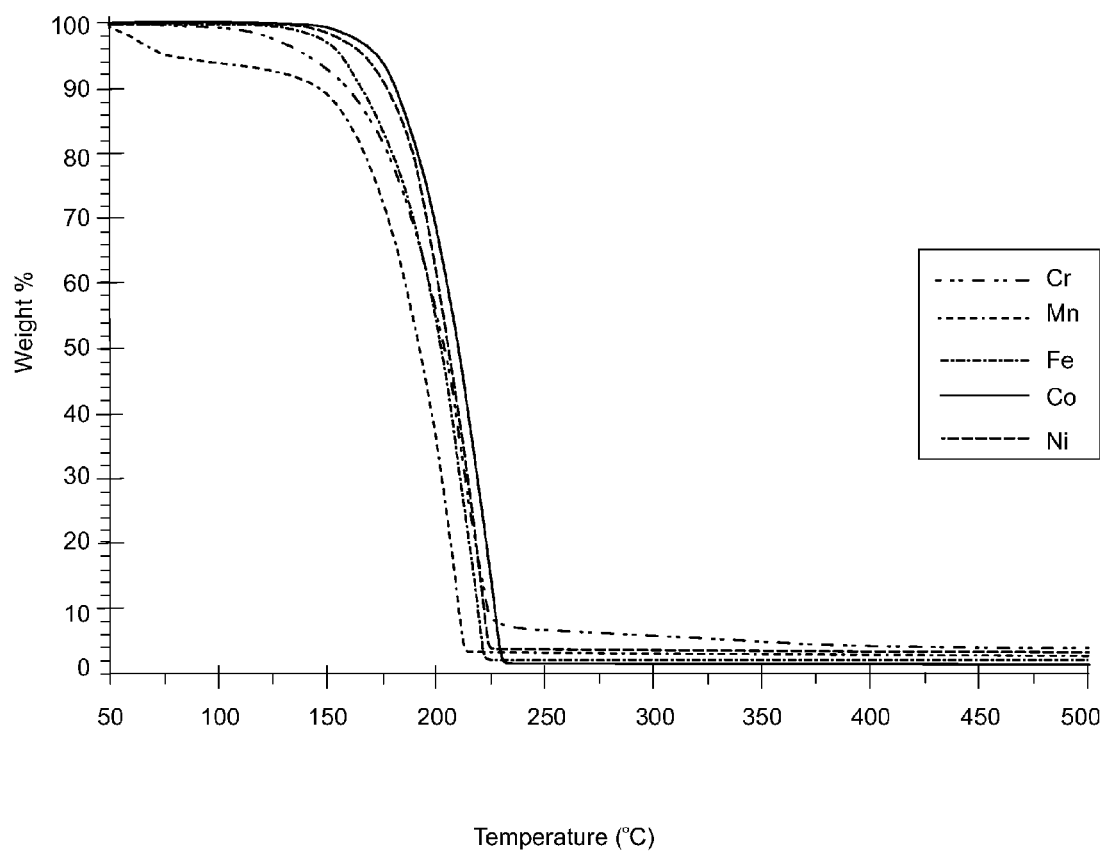
FIG. 11 provides thermogravimetric analysis traces of compounds 1-5 from 50 to 550° C. at 10° C./min.

Thermogravimetric analyses (TGA) were performed on 1-5 to understand their volatilities and thermal stabilities (FIG. 11). These analyses were carried out with an instrument that was contained in a high-purity nitrogen-filled glove box to minimize decomposition arising from exposure to air. Complexes 1-5 have similar TGA traces with single step weight losses occurring between 150 and 225° C. The residues upon reaching 500° C. were all ≤3.6%. Complex 2 is the most air sensitive compound in the series, and its TGA traces always showed 10-20% weight losses between 50 and 150° C. that were presumably due to reaction with ambient oxygen or water, in spite of multiple runs and utmost care to maintain a high purity nitrogen atmosphere.

Vapor pressure measurements were carried out on 2 and 5 using a previously reported method and apparatus. Details of these analyses are found in the Supporting Information. The vapor pressure of 2 obeys the equation $Log_{10}$ P(mTorr)=12.753−3631/T(K), whereas the equation for 5 is $Log_{10}$P(mTorr)=13.983−3986/T(K). The vapor pressures of 2 and 5 at 115° C. are 2.48 and 5.13 Torr, respectively. The vapor pressures of 1, 3, and 4 should be close to those of 2 and 5, since the preparative sublimation temperatures of 1-5 are similar.

Figure 12:
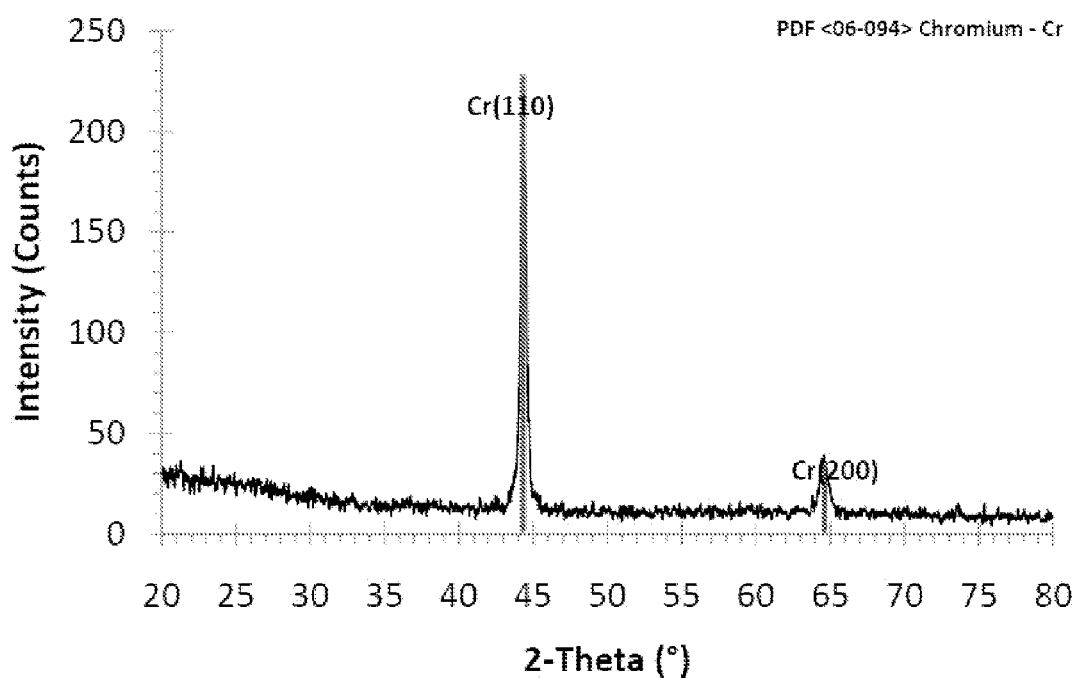
FIG. 12 provides an X-ray diffraction pattern of chromium metal powder obtained upon thermolysis of compound 1.

As described above, solid state decompositions of 1-5 afforded shiny metallic foils as products. To verify the formation of the metals, preparative scale solid state thermolyses were carried out on 1-5 as described in the Experimental Section and the residues were analyzed by X-ray powder diffraction. X-ray diffraction analyses demonstrated that 1 and 3-5 afford crystalline, shiny gray-black powders of the metals. FIG. 12 shows the X-ray diffraction pattern of the chromium metal thermolysis product from 1, which matches the JCPDS 06-0694 reference pattern for chromium metal. The X-ray diffraction patterns of the powders derived from 3-5 are contained in the Supporting Information. The thermolysis product of 2 was also a shiny metallic powder. The X-ray diffraction pattern of the thermolysis product obtained under conditions similar to those used for the thermolysis of 1 and 3-5 showed weak reflections that were consistent with Mn$_3$O$_4$ (JCPDS 04-07320). Since it was possible that the Mn$_3$O$_4$ formed upon oxidation of manganese metal by residual oxygen or water in the argon used in the thermolysis experiment, the thermolysis of 2 was repeated under a vacuum of 0.05 Torr at 375° C. for one hour. X-ray diffraction spectra of the resulting gray-black metallic powder did not show any reflections, suggesting an amorphous product. Treatment of the powders resulting from the thermolysis of 2 with 30% aqueous hydrogen peroxide led to vigorous reaction and gas evolution. Similar reactivities were observed for the powders resulting from thermolysis under flowing argon and under vacuum. For comparison, manganese metal powder reacted in a similar vigorous manner with 30% aqueous hydrogen peroxide, whereas commercial Mn$_3$O$_4$ powder was inert under the same conditions. The commercial Mn$_3$O$_4$ powder was crystalline and indexed as Hausmannite (JCPDS 24-0734), and is thus in a different crystalline form from the powder described above that was obtained upon thermolysis of 2. However, the reactivity of both forms of Mn$_3$O$_4$ toward 30% hydrogen peroxide should be similar. Hence, it is possible that thermolysis of 2 affords amorphous manganese metal powder.

Evaluation of Precursor Properties.

Complexes 1-5 sublime at 85 (1) and 115-120° C. (2-5) with low nonvolatile residues, have high solid state decomposition temperatures, and are highly reactive toward ambient atmosphere. Additionally, 1 and 3-5 decompose to the metals upon thermolysis, and 2 may afford manganese metal upon thermolysis. These complexes thus have useful properties for applications as film growth precursors by ALD and CVD. Complexes 1 and 3-5 decompose thermally between 230 and 295° C. to afford the metals, and 2 decomposes at 325° C. possibly to afford manganese metal. Since 1-5 evaporate with low residues between 85 and 120° C., they are highly likely to be useful CVD precursors to films of the metals. ALD precursors must be thermally stable at the film growth temperatures, or the self-limited ALD growth mechanism is lost and CVD-like growth occurs. Complexes 1-5 also have properties that may be useful in ALD film growth, especially since they have high thermal decomposition temperatures compared to other available precursors for each metal. For example, the amidinate complex Ni(iPrNC(Me)NiPr)$_2$ decomposes at about 180° C., compared to a solid state decomposition temperature of 235° C. for nickel complex 5. The amidinate complexes Fe(tBuNC(Me)NtBu)$_2$ and Co(iPrNC(Me)NiPr)$_2$ exhibited single step weight loss events in the TGA traces, but had 12% and 9% nonvolatile residues, respectively, upon reaching 225 (Fe(tBuNC(Me)NtBu)$_2$) and 200° C. (Co(iPrNC(Me)NiPr)$_2$). These nonvolatile residues are higher than those observed in the TGA traces of 1-5 (<3.6%), again suggesting that our new complexes have higher thermal decomposition temperatures than the analogous amidinate complexes. The increased thermal stabilities of 1-5 could allow wider temperature ranges of self-limited ALD film growth, relative to amidinate and other precursors with lower decomposition temperatures. ALD growth studies using 1-5 are ongoing, and will be reported separately.

Experimental Section

General Considerations

All manipulations were carried out under argon using either Schlenk or glove box techniques. Tetrahydrofuran was distilled from sodium benzophenone ketyl, and hexane was distilled from P$_2$O$_5$. Lithium metal was obtained from Acros Organics Anhydrous transition metal chlorides (CrCl$_2$, MnCl$_2$, FeCl$_2$, CoCl$_2$, and NiCl$_2$) were obtained from Strem Chemicals Inc. and used as received. Manganese metal powder and Mn$_3$O$_4$ were obtained from Aldrich Chemical Company. NiCl$_2$.CH$_3$CN[23] and 1,4-di-tert-butyl-1,3-diazabutadiene were prepared according to literature procedures.

$^1$H and $^{13}$C{$^1$H} NMR spectra were obtained at 400 and 100 MHz, respectively, in benzene-d$_6$ and were referenced to the residual proton and the $^{13}$C resonances of the solvent. Infrared spectra were obtained using Nujol as the medium. Magnetic moments were determined in the solid state using a Johnson Mathey magnetic susceptibility apparatus, and in benzene solution using the Evans method. Melting points were determined on a Thermo Scientific Mel-Temp 3.0 melting point apparatus and are uncorrected. X-ray quality crystals of 1 and 3-5 were grown from hexane at −23° C. Preparative sublimations and solid state decomposition temperatures were determined using previously described procedures. Thermogravimetric analyses were performed in a nitrogen filled glove box on a TA Instruments Q500 equipped with an evolved gas analysis furnace with samples heated at a rate of 10° C./min. Elemental analyses were performed by Midwest Microlab, Indianapolis, Ind. Powder X-ray diffraction data was acquired on a Rigaku RU200B diffractometer with a Cu Kα rotating anode. Crystalline phases were identified by comparison of the experimental patterns with the powder diffraction files of the International Center of Diffraction Data using the Jade 5.0 software package.

Preparation of Bis(1,4-di-tert-butyl-1,3-diazabutadienyl)chromium(II) (1)

A 100 mL Schlenk flask, equipped with a magnetic stir bar and a rubber septum, was charged with 1,4-di-tert-butyl-1,3-diazabutadiene (1.000 g, 5.94 mmol) and tetrahydrofuran (20 mL). To this stirred solution at ambient temperature was slowly added freshly cut lithium metal (0.042 g, 6.000 mmol) and the resultant dark brown solution was stirred for 6 h. This solution was then added dropwise by cannula over a 30 min period to a stirred suspension of anhydrous chromium(II) chloride (0.365 g, 2.970 mmol) in tetrahydrofuran (40 mL). The resultant deep purple solution was stirred for 6 h at ambient temperature. The volatile components were then removed under reduced pressure and the resultant dark purple powder was dissolved in toluene (50 mL). The solution was filtered through a 1-cm pad of Celite on a coarse glass frit, and toluene was then removed under reduced pressure. Dark purple crystals of 1 were obtained by sublimation at 85° C./0.05 Torr (0.442 g, 38%): mp 95-97° C.; IR (Nujol, cm$^{-1}$) 1704 (w), 1628 (w), 1538 (w), 1246 (m), 1209 (s), 1132 (m), 1104 (m), 1034 (m); $\mu_{eff}$=2.83 and 2.84 BM in the solid state and in benzene solution, respectively. Anal. Calcd for C$_{20}$H$_{40}$CrN$_4$: C, 61.82; H, 10.38; N, 14.42. Found: C, 61.71; H, 10.06; N, 14.37.

Preparation of Bis(1,4-di-tert-butyl-1,3-diazabutadienyl)manganese(II) (2)

In a fashion similar to the preparation of 1, treatment of anhydrous MnCl$_2$ (0.371 g, 2.970 mmol) in tetrahydrofuran (40 mL) with a solution of Li$^{tBu2}$DAD (prepared from 1,4-di-tert-butyl-1,3-diazabutadiene (1.000 g, 5.940 mmol) and freshly cut lithium metal (0.042 g, 6.000 mmol) in tetrahydrofuran (20 mL)) for 6 h at ambient temperature afforded 2 (0.942 g, 81%) as black crystals upon sublimation at 120° C./0.05 Torr: mp 155-157° C.; IR (Nujol, cm$^{-1}$) 1716 (m), 1610 (m), 1558 (w), 1364 (s), 1254 (s), 1210 (s), 1007 (m), 929 (m), 759 (s); $^1$H NMR (C$_6$D$_6$, 23° C., δ) 8.06 (s, broad, CH), 1.10 (s, very broad, C(CH$_3$)$_3$); $\mu_{eff}$=3.85 and 3.85 BM in the solid state and in benzene solution, respectively. Anal. Calcd for C$_{20}$H$_{40}$MnN$_4$: C, 61.36; H, 10.30; N, 14.31. Found: C, 60.99; H, 9.96; N, 14.01.

Preparation of Bis(1,4-di-tert-butyl-1,3-diazabutadienyl)iron(II) (3)

In a fashion similar to the preparation of 1, treatment of anhydrous FeCl$_2$ (0.377 g, 2.970 mmol) in tetrahydrofuran (40 mL) with Li$^{tBu2}$DAD (prepared from 1,4-di-tert-butyl-1,3-diazabutadiene (1.000 g, 5.940 mmol) and freshly cut lithium metal (0.042 g, 6.000 mmol) in tetrahydrofuran (20 mL)) for 6 h at ambient temperature afforded 3 (0.544 g, 47%) as dark brown crystals upon sublimation at 110° C./0.05 Torr: mp 132-134° C.; IR (Nujol, cm$^{-1}$) 1703 (w), 1606 (w), 1525 (w), 1359 (s), 1254 (s), 1208 (s), 1022 (m), 1002 (m), 926 (m), 762 (s); $\mu_{eff}$=2.88 and 2.68 BM in the solid state and in benzene solution, respectively. Anal. Calcd for C$_{20}$H$_{40}$FeN$_4$: C, 61.22; H, 10.27; N, 14.16. Found: C, 61.39; H, 10.03; N, 14.16.

Preparation of Bis(1,4-di-tert-butyl-1,3-diazabutadienyl)cobalt(II) (4)

In a fashion similar to the preparation of 1, treatment of anhydrous $CoCl_2$ (0.386 g, 2.970 mmol) in tetrahydrofuran (40 mL) with $Li^{tBu2}DAD$ (prepared from 1,4-di-tert-butyl-1,3-diazabutadiene (1.000 g, 5.940 mmol) and freshly cut lithium metal (0.042 g, 6.000 mmol) in tetrahydrofuran (20 mL)) for 6 h at ambient temperature afforded 4 (0.418 g, 36%) as dark-blue crystals upon sublimation at 110° C./0.05 Torr: mp 173-174° C.; IR (Nujol, $cm^{-1}$) 1698 (m), 1605 (m), 1527 (m), 1362 (s), 1260 (s), 1210 (s), 1008 (s), 933 (m), 763 (s); $\mu_{eff}$=1.75 and 1.83 BM in the solid state and in benzene solution, respectively. Anal. Calcd for $C_{20}H_{40}CoN_4$: C, 60.74; H, 10.19; N, 14.17. Found: C, 60.84; H, 10.01; N, 14.29.

Preparation of Bis(1,4-di-tert-butyl-1,3-diazabutadienyl)nickel(II) (5)

In a fashion similar to the preparation of 1, treatment of $NiCl_2.CH_3CN$ (0.507 g, 2.970 mmol) in tetrahydrofuran (40 mL) with $Li^{tBu2}DAD$ (prepared from 1,4-di-tert-butyl-1,3-diazabutadiene (1.000 g, 5.940 mmol) and freshly cut lithium metal (0.042 g, 6.000 mmol) in tetrahydrofuran (20 mL)) for 6 h at ambient temperature afforded 5 (0.482 g, 41%) as dichroic red-green crystals upon sublimation at 110° C./0.05 Torr: mp 184-185° C.; IR (Nujol, $cm^{-1}$) 1715 (w), 1625 (w), 1547 (w), 1493 (s), 1264 (s), 1212 (s), 934 (m), 764 (s); $^1H$ NMR ($C_6D_6$, 23° C., δ) 8.95 (s, 2H, CH), 1.93 (s, 18H, $C(CH_3)_3$); $^{13}C\{^1H\}$ NMR ($C_6D_6$, 23° C., ppm) 129.88 (s, CH), 64.61 (s, $C(CH_3)_3$), 30.61 (s, $C(CH_3)_3$). Anal. Calcd for $C_{20}H_{40}N_4Ni$: C, 60.77; H, 10.20; N, 14.85. Found: C, 60.89; H, 9.88; N, 14.61.

Solid State Thermolyses of 1-5.

Thermolysis experiments were performed on analytically pure samples of 1-5 to assess their solid state thermal decomposition products. A 20-cm long, 2.5-cm diameter quartz tube, equipped with female 24/40 joints on each end, was fitted with two flow control valves that were attached to male 24/40 joints. A 6-cm long, 1-cm diameter glass vial was charged with 1.00 g of the sample in a glove box. The vial was placed in the center of the quartz tube. This apparatus was placed into a tube furnace and a 50 sccm flow of argon was established. The sample was then heated to 500° C. for 1 h and was allowed to cool to room temperature under argon flow. Subsequently, the powder residues were collected from the inside of the quartz tube and subjected to X-ray powder diffraction analyses as described in the text.

X-ray Crystallographic Structure Determinations.

Diffraction data were measured on a Bruker X8 APEX-II kappa geometry diffractometer with Mo radiation and a graphite monochromator. Frames were collected at 100 K with the detector at 40 mm and 0.3-0.5° between each frame. The frames were recorded for 3-5 s. APEX-II and SHELX software were used in the collection and refinement of the models. All structures contained discrete neutral complexes without ions or solvent. Complex 1 crystallized with two independent but chemically equivalent molecules in the asymmetric unit. Complexes 3-5 are all isostructural, with one-half molecule in the asymmetric unit. The iron, cobalt and nickel atoms all occupy a crystallographic mirror plane.

DEPOSITION EXAMPLES

Example 1

The activating compound is a coreagent where the resulting thin film would be a metallic. For example, reacting complexes 1-5 with diethylsilane induces reduction of the transition metal to produce a metal film. In addition, metallic film formation occurs by reducing metal nitride films under inert/reducing atmospheres at elevated temperatures. For example, $Ni_3N$ is reduced to nickel metal when heated above 180° C. under a $H_2$ atmosphere. Additionally, when complexes 1-5 are reacted with formic acid upon a catalytically active ruthenium substrate, catalytic decomposition of the metal formate to the respective metal occurs.

Example 2

The activating compound is a nitrogen-based coreagent where the resulting thin film would be a transition metal nitride. Useful sources of nitrogen-based coreagents include ammonia, hydrazine, dimethylhydrazine, and plasma-activated versions thereof. When complexes 1-5 are reacted with dimethyl hydrazine, metal nitride films will be formed. Ammonia and other nitrogen sources will produce nitrides as well.

Example 3

The activating compound is an oxidizing agent resulting in the formation of a metal oxide thin film. Given their high reactivity toward ambient dioxygen and water, 1-5 will decompose to the respective metal oxides. Therefore, combining this practice to film growth using a combination of 1-5 and an oxygen source such as oxygen or ozone, a metal oxide film will be produced.

Example 4

Figure 13:
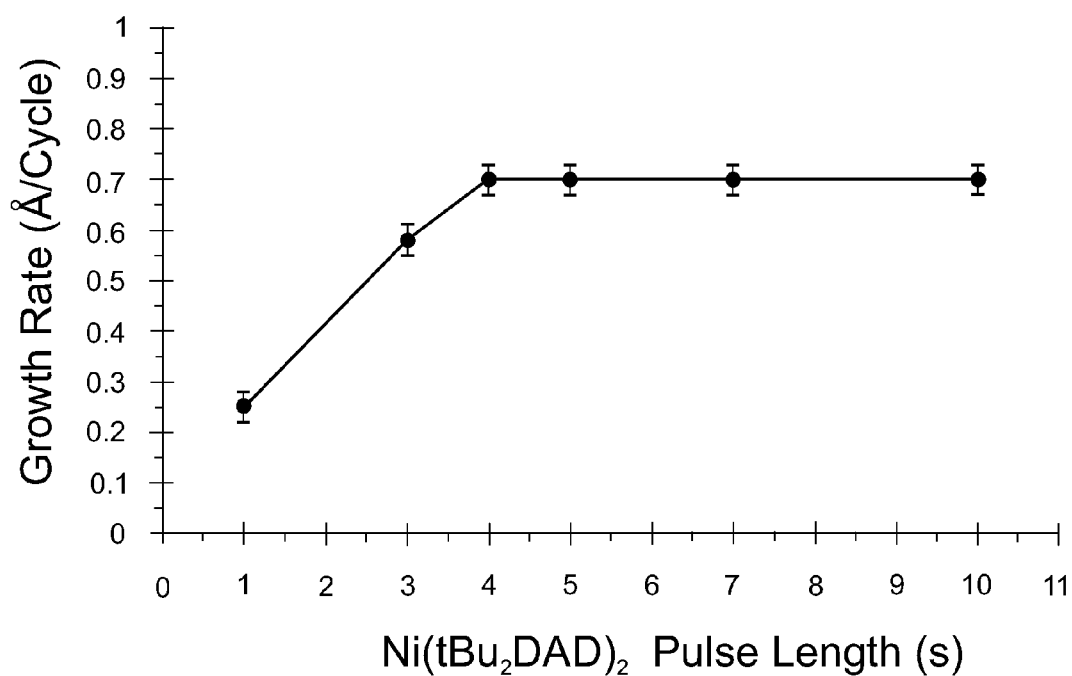
FIG. 13 provides a plot of growth rate as a function of $Ni(tBu_2DAD)_2$ pulse length at a substrate temperature of 225° C.

ALD growth of $Ni_xN$ on 500 nm thick thermal $SiO_2$ was investigated using complex 5 and anhydrous 1,1-dimethylhydrazine. The growth of $Ni_xN$ was evaluated by varying substrate temperatures, precursor pulse lengths, and the number of deposition cycles. The study of growth rate as a function of $Ni(tBu_2DAD)_2$ (complex 5) pulse length was carried out at a substrate temperature of 225° C. (FIG. 13). The 1,1-dimethylhydrazine pulse length, purge time between each reactant, and the number of deposition cycles were held constant at 0.2 s, 3.0 s, and 1000 cycles, respectively. The complex 5 source was kept at 150° C. to allow for sufficient consumption of the precursor over the deposition period. In order to display that film growth is occurring by a self-limited ALD mechanism, film saturation must be demonstrated. In the event of surface saturation, all available surface sites are occupied with adsorbed precursor molecules, which in turn remain on the film surface awaiting the introduction of a second coreactant. Once this condition is met, a constant growth rate is observed even in cases of excess precursor dose, given that neither precursor undergoes thermal decomposition. Self-limited film growth was achieved with complex 5 pulse lengths ≥4.0 s as evident by a constant growth rate of 0.7 Å/cycle when these conditions were met. Shorter pulse lengths of complex 5 (<4 s) may lead to sub-saturative growth and loss of the self-limiting ALD mechanism. For the studies described herein, a complex 5 pulse length of 4.0 s was applied to guarantee self-limited film growth. A plot of growth rate versus 1,1-dimethylhydrazine pulse length exhibited similar saturative behavior at pulse lengths ≥0.2 s.

Figure 14:
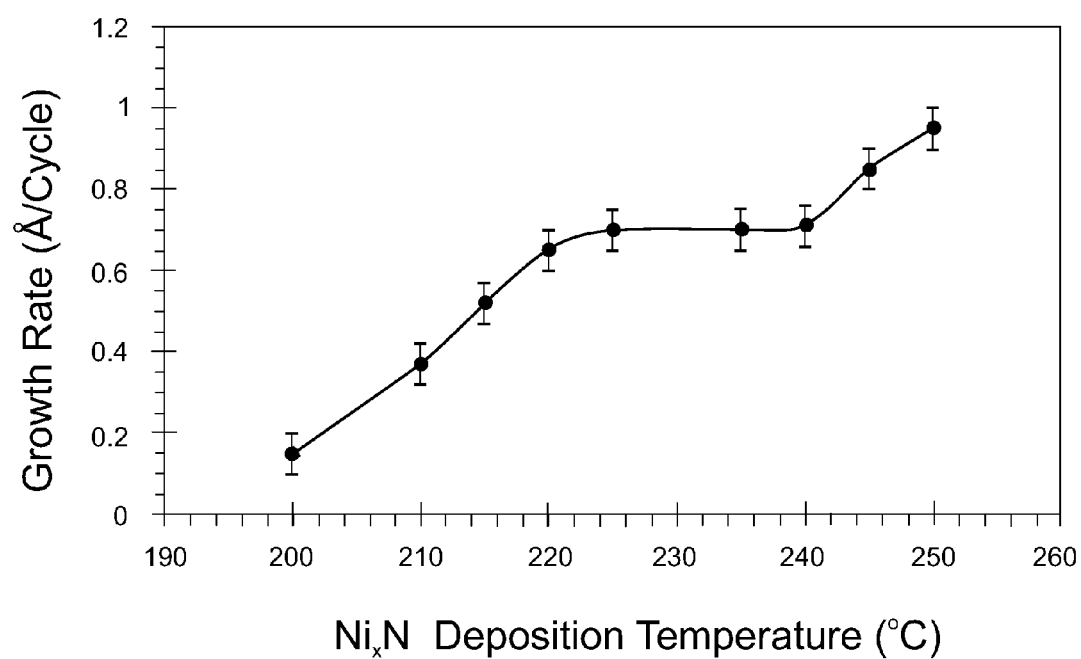
FIG. 14 provides a plot of growth rate as a function of deposition temperature. (An ALD window is observed between 225 and 240° C.)

The effect of substrate temperature upon growth rate was also investigated (FIG. 14). Film depositions were executed using complex 5 and 1,1-dimethylhydrazine pulse lengths of 5.0 s, 0.2 s, and 1000 deposition cycles. Nitrogen purge times of 3.0 s were used between each reactant pulse. A consistent growth rate of 0.7 Å/cycle was obtained between 225 and 240° C. This observed region of constant growth rate over a specified temperature range is often referred to as the "ALD window" and is further evidence of an ALD process. Interestingly, the observed ALD window extends up to 240° C., which lies beyond the decomposition temperature of complex 5. It is also noted that at substrate temperatures ≥240° C., the growth rate increases significantly due to precursor decomposition. Ni$_x$N growth rates of 0.15 and 0.95 Å/cycle were observed at substrate temperatures of 200 and 250° C., respectively, which extend beyond the observed ALD window.

Figure 15:
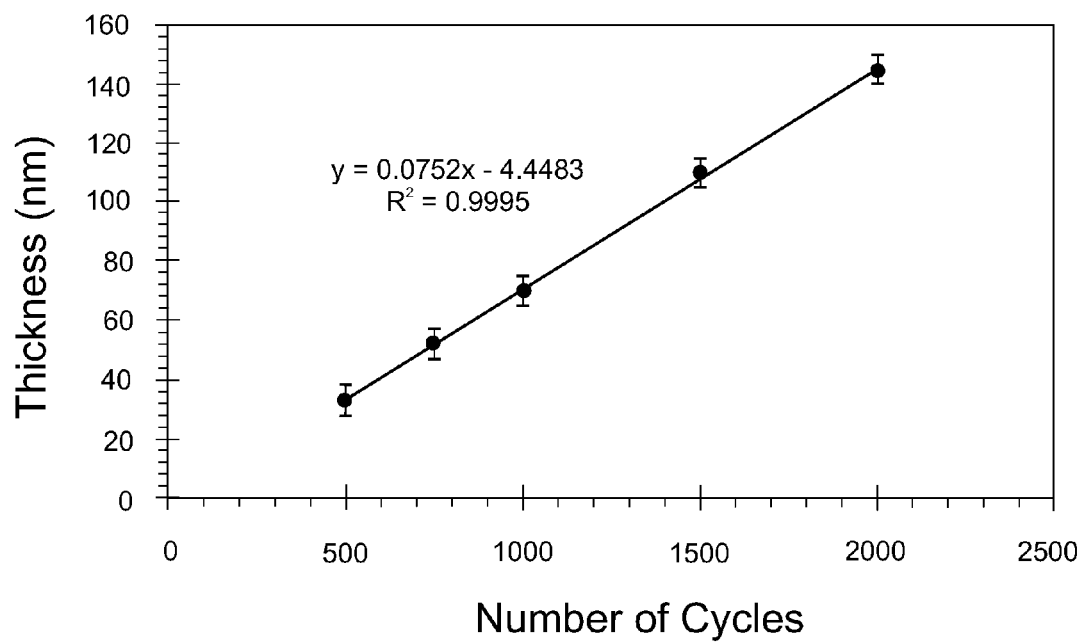
FIG. 15 provides a plot of film thickness as a function of the number of deposition cycles at a growth temperature of 225° C.

The influence of the number of deposition cycles upon the film thickness of NixN was subsequently investigated. In this collection of experiments, the complex 5 and 1,1-dimethylhydrazine pulse lengths were kept at 4.0 and 0.2 s, respectively, with a 3.0 s inert gas purge between each reactant pulse. The substrate temperature was held at 225° C. The thickness of the film varied in a direct linear behavior with respect to the number of ALD cycles employed as shown in FIG. 15. A trendline that demonstrates a best fit for the data points collected has a y-intercept of 4.45 nm. In principle, the y-intercept should be zero or negative which would indicate an incubation period. In this case, the positive y-intercept value could be attributed to a minor artificial offset induced from the observed film roughness and its effects on thickness measurements as determined by cross sectional SEM.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for depositing a thin film on a surface of a substrate, the method comprising:
   a) contacting the substrate with a vapor of a metal-containing compound to form a modified surface on the substrate, the metal-containing compound being described by formula II:

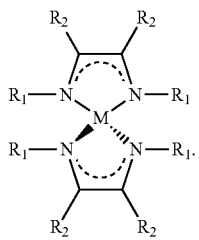

II wherein
   M is Mn(II), Fe(II), Co(II), or Ni(II);
   $R_1$ is $C_1$-$C_{12}$ alkyl, amine, or $C_6$-$C_{18}$ aryl; and
   $R_2$ is hydrogen, $C_1$-$C_{10}$ alkyl, $C_6$-$C_{18}$ aryl, amino, $C_1$-$C_{12}$ alkylamino, or $C_2$-$C_{24}$ dialkylamino; and
   b) contacting the modified surface with a vapor of an activating compound to form at least a portion of the thin film on the surface of the substrate.

2. The method of claim 1 wherein the activating compound is a reducing agent and the thin film is a metallic film.

3. The method of claim 2 wherein the reducing agent is selected from the group consisting of molecular hydrogen, atomic hydrogen, silane, disilane, organosilanes, compounds containing Si—H bonds, germane, organogermanes, compounds containing Ge—H bonds, stannane, compounds containing Sn—H bonds, other metal hydride compounds, formic acid, glyoxalic acid, oxalic acid, other carboxylic acids, diborane, compounds containing B—H bonds, hydrazine, carbon-substituted hydrazines, formalin, formaldehyde, organic alcohols, organoaluminum compounds, organozinc compounds, and plasma-activated versions thereof.

4. The method of claim 1 wherein the activating compound is an oxidizing agent and the thin film is a metal oxide.

5. The method of claim 4 wherein the oxidizing agent is selected from the group consisting of water, ozone, molecular oxygen, atomic oxygen, organic alcohols, hydrogen peroxide, organic hydroperoxides, organic peroxides, nitrous oxide, and plasma-activated versions of thereof.

6. The method of claim 1 wherein the activating compound is a nitrogen-containing agent and the thin film is a metal nitride.

7. The method of claim 6 wherein the activating compound is selected from the group consisting of ammonia, hydrazine, alkyl-substituted hydrazines, and plasma activated versions thereof.

8. The method of claim 1 wherein the compound having formula II is thermally activated.

9. The method of claim 1 wherein the compound having formula II is plasma activated.

10. The method of claim 1 wherein $R_1$ and $R_2$ are each independently $C_1$-$C_4$ alkyl.

11. The method of claim 1 wherein $R_1$ and $R_2$ are each independently methyl, ethyl, propyl, n-butyl, sec-butyl, isobutyl, or t-butyl.

12. The method of claim 1 wherein $R_1$ is t-butyl.

13. The method of claim 1 wherein M is Fe(II), Co(II), or Ni(II).

14. The method of claim 1 wherein M is Mn(II), Co(II), or Ni(II).

15. The method of claim 1 wherein M is Co(II).

16. The method of claim 1 wherein M is Mn(II).

17. The method of claim 1 wherein M is Ni(II).

18. The method of claim 1 wherein M is Fe(II).

* * * * *